(12) United States Patent
Lynch et al.

(10) Patent No.: US 8,343,115 B2
(45) Date of Patent: *Jan. 1, 2013

(54) LOW PROFILE PIVOTING JOINT INFUSION ASSEMBLY

(75) Inventors: George R. Lynch, Coppell, TX (US); Andrew Nelson, Dallas, TX (US); Gilles Petitjean, Issoudun (FR)

(73) Assignee: Applied Diabetes Research, Inc., Carrollton, TX (US)

( * ) Notice: Subject to any disclaimer, the term of this patent is extended or adjusted under 35 U.S.C. 154(b) by 272 days.

This patent is subject to a terminal disclaimer.

(21) Appl. No.: 12/534,274

(22) Filed: Aug. 3, 2009

(65) Prior Publication Data

US 2009/0299299 A1    Dec. 3, 2009

Related U.S. Application Data

(63) Continuation of application No. 10/333,499, filed as application No. PCT/US02/00128 on Jan. 4, 2002, now Pat. No. 7,569,034, and a continuation-in-part of application No. 09/896,149, filed on Jun. 29, 2001, now Pat. No. 6,579,267.

(60) Provisional application No. 60/259,971, filed on Jan. 5, 2001.

(51) Int. Cl.
*A61M 37/00* (2006.01)
(52) U.S. Cl. .................................. 604/288.03
(58) Field of Classification Search .................. 604/246, 604/288.03
See application file for complete search history.

(56) References Cited

U.S. PATENT DOCUMENTS

| 3,547,119 | A | 12/1970 | Niles et al. |
| 3,739,778 | A | 6/1973 | Monestere, Jr. et al. |
| 3,996,923 | A | 12/1976 | Guerra |
| 4,106,491 | A | 8/1978 | Guerra |
| 4,126,133 | A | 11/1978 | Schwartz |
| 4,258,940 | A | 3/1981 | Fudge |

(Continued)

FOREIGN PATENT DOCUMENTS

FR    2578746 A1    9/1986

OTHER PUBLICATIONS

American National Standard ANSI/HIMA MD70.1-1983, Dimensional Requirements for Luer Lock Fittings, Figure 7, p. 12.

(Continued)

*Primary Examiner* — Kevin C Sirmons
*Assistant Examiner* — Deanna K Hall
(74) *Attorney, Agent, or Firm* — Jackson Walker, LLP

(57) ABSTRACT

System for the subcutaneous delivery into the body of a patient of a fluid from a remote vessel. The system includes a main assembly and placement member with a needle. A delivery tube for carrying the fluid is attached at a near end to the remote reservoir or vessel. At removed end, the delivery tube has a needle for engagement with the main assembly. The main assembly includes a rotating member that when the rotating is perpendicular to the main assembly, it will accept the handle and needle for emplacement of the body onto a patient. After the handle and needle are removed, the delivery tube can be attached to the rotating member which can then be rotated down to a position along to and adjacent the skin of the patient. This provides for a flush mounted infusion device.

20 Claims, 20 Drawing Sheets

U.S. PATENT DOCUMENTS

| | | | |
|---|---|---|---|
| 4,311,136 A | 1/1982 | Weikl et al. | |
| 4,311,137 A | 1/1982 | Gerard | |
| 4,418,944 A | 12/1983 | Haines et al. | |
| 4,430,081 A | 2/1984 | Timmermans | |
| 4,531,937 A | 7/1985 | Yates | |
| 4,645,495 A | 2/1987 | Vaillancourt | |
| 4,755,173 A | 7/1988 | Konopka et al. | |
| 4,936,833 A | 6/1990 | Sams | |
| 5,019,054 A | 5/1991 | Clement et al. | |
| 5,098,394 A | 3/1992 | Luther | |
| 5,176,662 A | 1/1993 | Bartholomew et al. | |
| 5,201,717 A | 4/1993 | Wyatt et al. | |
| 5,242,411 A | 9/1993 | Yamamoto | |
| 5,257,980 A | 11/1993 | Van Antwerp et al. | |
| 5,281,206 A | 1/1994 | Lopez | |
| 5,300,045 A | 4/1994 | Plassche, Jr. | |
| 5,330,450 A | 7/1994 | Lopez | |
| 5,376,071 A | 12/1994 | Henderson | |
| 5,427,145 A | 6/1995 | Grabenkort | |
| 5,545,143 A | 8/1996 | Fischell | |
| 5,545,152 A | 8/1996 | Funderburk et al. | |
| 5,613,663 A | 3/1997 | Schmidt et al. | |
| 5,814,020 A | 9/1998 | Gross | |
| 5,848,990 A | 12/1998 | Cirelli et al. | |
| 5,851,197 A | 12/1998 | Marano et al. | |
| D404,482 S | 1/1999 | Falk et al. | |
| 5,858,001 A | 1/1999 | Tsais et al. | |
| 5,968,011 A | 10/1999 | Larsen et al. | |
| 5,980,506 A | 11/1999 | Mathiasen | |
| 6,017,328 A | 1/2000 | Fischell et al. | |
| 6,056,718 A | 5/2000 | Funderburk et al. | |
| 6,093,172 A | 7/2000 | Funderburk et al. | |
| 6,095,997 A | 8/2000 | French et al. | |
| 6,186,982 B1 | 2/2001 | Gross et al. | |
| 6,213,973 B1 | 4/2001 | Eliasen et al. | |
| 6,248,093 B1 | 6/2001 | Moberg | |
| 6,302,866 B1 | 10/2001 | Marggi | |
| 6,355,021 B1 | 3/2002 | Nielsen et al. | |
| 6,419,699 B1 | 7/2002 | Schuessler | |
| 6,482,186 B1 | 11/2002 | Douglas et al. | |
| D471,272 S | 3/2003 | Douglas et al. | |
| D472,316 S | 3/2003 | Douglas et al. | |
| D472,630 S | 4/2003 | Douglas et al. | |
| 6,579,267 B2 * | 6/2003 | Lynch et al. | 604/174 |
| 6,585,695 B1 | 7/2003 | Adair et al. | |
| 6,629,949 B1 | 10/2003 | Douglas | |
| 6,641,566 B2 | 11/2003 | Douglas et al. | |
| 6,659,982 B2 | 12/2003 | Douglas et al. | |
| 6,673,440 B2 | 1/2004 | Douglas et al. | |
| 6,685,674 B2 | 2/2004 | Douglas et al. | |
| D488,230 S | 4/2004 | Ignotz et al. | |
| 6,752,787 B1 | 6/2004 | Causey, III et al. | |
| 6,800,071 B1 | 10/2004 | McConnell et al. | |
| 6,817,990 B2 | 11/2004 | Yap et al. | |
| 6,854,620 B2 | 2/2005 | Ramey | |
| 6,854,809 B1 | 2/2005 | Ramey | |
| 6,923,791 B2 | 8/2005 | Douglas | |
| 7,056,302 B2 | 6/2006 | Douglas | |
| 7,063,684 B2 | 6/2006 | Moberg | |
| 7,083,597 B2 * | 8/2006 | Lynch et al. | 604/174 |
| 7,211,068 B2 | 5/2007 | Douglas | |
| 7,569,034 B2 * | 8/2009 | Lynch et al. | 604/174 |
| 7,766,867 B2 * | 8/2010 | Lynch et al. | 604/93.01 |
| 2002/0045867 A1 | 4/2002 | Nielsen et al. | |
| 2002/0123724 A1 | 9/2002 | Douglas et al. | |
| 2002/0173748 A1 | 11/2002 | McConnell et al. | |
| 2003/0125672 A1 | 7/2003 | Adair et al. | |
| 2003/0163090 A1 | 8/2003 | Blomquist et al. | |
| 2004/0003493 A1 | 1/2004 | Adair et al. | |
| 2004/0085215 A1 | 5/2004 | Moberg et al. | |
| 2004/0092873 A1 | 5/2004 | Moberg | |
| 2005/0021000 A1 | 1/2005 | Adair et al. | |

OTHER PUBLICATIONS

American National Standard ANSI/HIMA MD70.1-1983, Dimensional Requirements for Luer Fittings, Figure 7, p. 12.

Medtronic MiniMed Paradigm Reservoir, 3 ml, Ref MMT-332A, User Guide.

* cited by examiner

LOW PROFILE PIVOTING JOINT INFUSION ASSEMBLY

This application is a continuation of U.S. patent application Ser. No. 10/333,499, which was filed on Jan. 17, 2006, and is now issued as U.S. Pat. No. 7,569,034, which is a national stage of PCT/US02/00128, which was filed on Jan. 4, 2002, and is a continuation-in-part of U.S. patent application Ser. No. 09/896,149, which was filed on Jun. 29, 2001 and is now issued as U.S. Pat. No. 6,579,267, which claims priority to U.S. Provisional Application No. 60/259,971, which was filed on Jan. 5, 2001, all of which are herein incorporated by reference.

BACKGROUND OF THE INVENTION

The instant low profile, pivoting joint infusion assembly transports therapeutic fluids, such as insulin, from a remote, external source to a subcutaneous location in a patient's body with little or no leakage of fluids. The therapeutic fluid passes from the source, through a delivery tube, to a fluid infusion connection unit removably attachable to a therapeutic fluid infusion unit designed to be affixed to the patient's skin. The fluid infusion unit has a cannula insertable approximately normal to the skin to subcutaneously deliver the therapeutic fluid within the patient.

As is well known in the art, the cannula is generally a hollow, soft, flexible member which enters the skin through a passageway formed by a hollow sharp-tipped, insertion needle. The insertion needle pierces the skin and subcutaneous regions of the infusion site allowing the cannula to pass therethrough. The needle is removed and properly disposed. Once the fluid infusion unit is connected to the patient, it generally remains in position. The connector assembly may be attached/detached as necessary to replace or change the therapeutic fluid being administered.

In the various embodiments of the present invention, a rotating member ensures accurate, positive alignment of fluid paths through the connection unit and the infusion unit.

Numerous approaches have been taken to provide quick-disconnect system for infusion therapy. U.S. Pat. Nos. 5,545,143 and 6,017,328 to Fishell disclose and teach such prior art systems. However, there are considerable drawbacks to the prior art systems; namely, the high cost of manufacturing an integral septum system within the main body or fluid infusion unit and the necessity for removably attaching the connector assembly through the top surface of fluid infusion unit, thereby creating a higher profile for the entire infusion assembly when worn by the patient. It is well known that the higher the assembly's profile the more likely the assembly may be disturbed, exposed to unintentionally external contact, and dislodgment from the infusion site. Further, to ensure a leak-free infusion system, it is critical that there be positive alignment of the fluid infusion unit and the fluid connection assembly.

The various embodiments of the present invention solve the long-standing problems of the prior art devices. They achieve improved infusion therapies by, among other things, providing a safe, low-profile assembly wherein the therapeutic fluids may be administered, replaced, and changed quickly, securely, and confidently in an extremely low-damage exposure arrangement with little or no leakage of the therapeutic fluids to the environment.

DETAILED DESCRIPTION OF THE PREFERRED EMBODIMENTS

Figure 1:
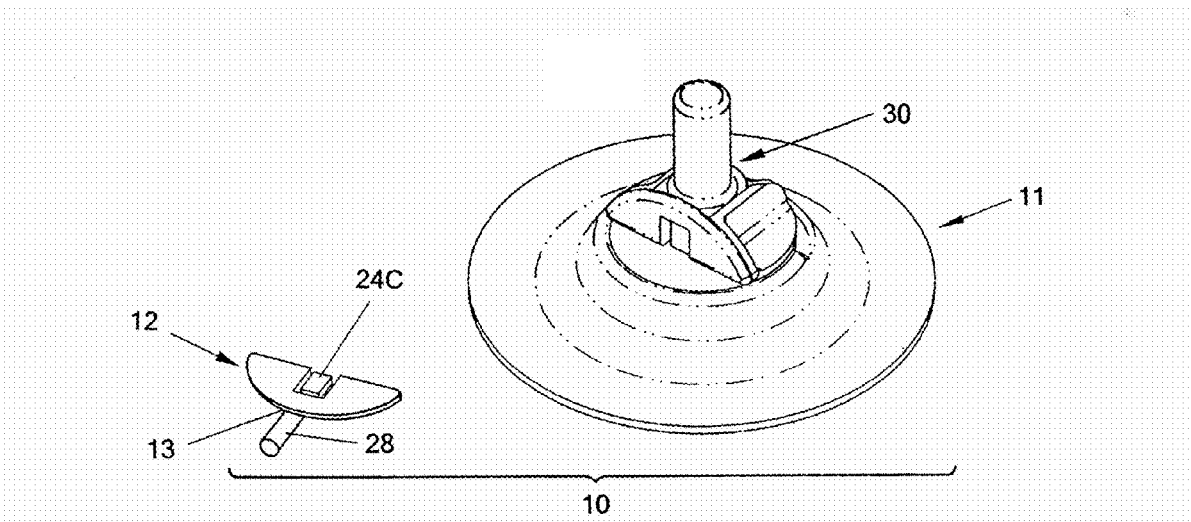
FIG. 1 is a perspective view of one embodiment of the present system for the subcutaneous delivery of a therapeutic fluid showing the infusion unit with the emplacement member attached and showing the fluid infusion connection unit ready for attachment to the infusion unit.

FIG. 1 illustrates a first embodiment of the present invention showing the pivoting joint infusion assembly 10 having a main fluid infusion unit 11 and an infusion fluid connection unit 24. The fluid infusion unit 11 is shown in FIG. 1 with a main fluid infusion unit emplacement member 30 attached to the unit 11 as would be the situation when the unit is ready for placement on the patient's body. The connection unit 24 is shown with a portion of the fluid delivery tube 28 attached to the first end 13 of the connection unit 24. Opposite the first end is a rotating member attachment portion 24C which may be connected to the infusion unit after the emplacement member is withdrawn.

Figure 1A:
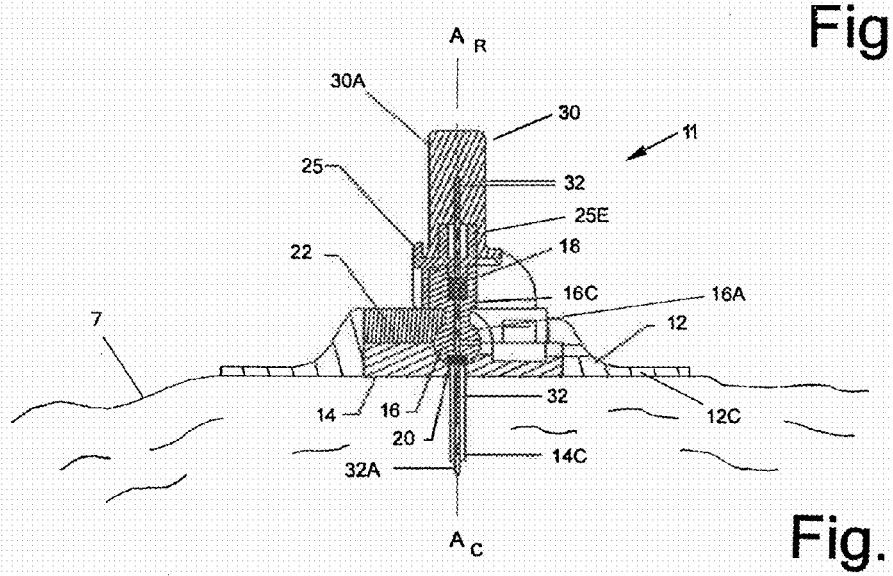
FIG. 1A is a cross-sectional side elevation view of one embodiment of the infusion unit on the skin of the patient with the emplacement member attached.

FIG. 1A shows a cross-sectional, side elevation view of the main fluid infusion unit 11 with the emplacement member 30 attached thereto. FIG. 1A shows the assembly 10 in a first emplacement position. The emplacement member 30 has a head section 30A with an insertion needle 32 securely attached to the head section. The distal end 32A of the needle extends through the main fluid infusion unit 11 and extends beyond the distal end of the downwardly depending cannula 14C attached to the underside 12C of the infusion unit 11. Cannula 14C has longitudinal cannula axis $A_C$. In order to attach the infusion unit 11 to the patient, the underside 12C (generally having an adhesive applied thereto) is pressed against the patient's skin 7 with the needle 32 puncturing the skin and allowing the cannula 14C to slide subcutaneously into the infusion site. The emplacement member 30 is then withdrawn and discarded, including the needle 32, and the infusion unit 11 remains in place with the cannula 14C in fluid communication with the patient's body.

Infusion unit 11 has a main assembly body 12 as seen in FIG. 1A. Cooperating with the main assembly body 12 is a base 14 into which seats a rotating member or pivoting joint 16 overlain at a first end 16A with a joint retaining cover 22. Rotating member 16 also has an engagement arm 16C for receiving the rotating member engagement portion 24C of the infusion fluid connection unit 24 as will be discussed below. Engagement arm 16C has a longitudinal arm axis, $A_R$.

Turning again to the base 14, it is insertable through the underside 12C of the body 12 whereby it cooperates with the joint retaining cover 22 to "sandwich" or enclose the first end 16A of rotating member 16. Thus, the base and cover have complimenting inner arcuate surfaces to allow the joint 16 to pivot. In the embodiment of FIG. 1A, the joint 16 includes a first septum 18 and a second septum 20. The first septum 18, after removal of the emplacement member needle 32, will eventually receive a delivery needle 26 on the fluid connection unit 24. This will allow for delivery of the therapeutic fluid from the remote source into the rotating member 16 then through the cannula 14C and into the patient's body. As will be seen below, not all embodiments of the present invention require the fluid to pass through the rotating member 16.

FIG. 1A shows the insertion needle 32 penetrating the first septum 18; extending through the engagement arm 16 along longitudinal arm axis $A_R$; penetrating the second septum 20; continuing through the cannula along the longitudinal cannula axis $A_C$; extending beyond the distal end of the cannuala; and penetrating into the patient's subcutaneous tissue. A plug 25 engages the engagement arm 16C of the rotating member 16 and acts as a guide for receipt of emplacement member 30.

Figure 2:
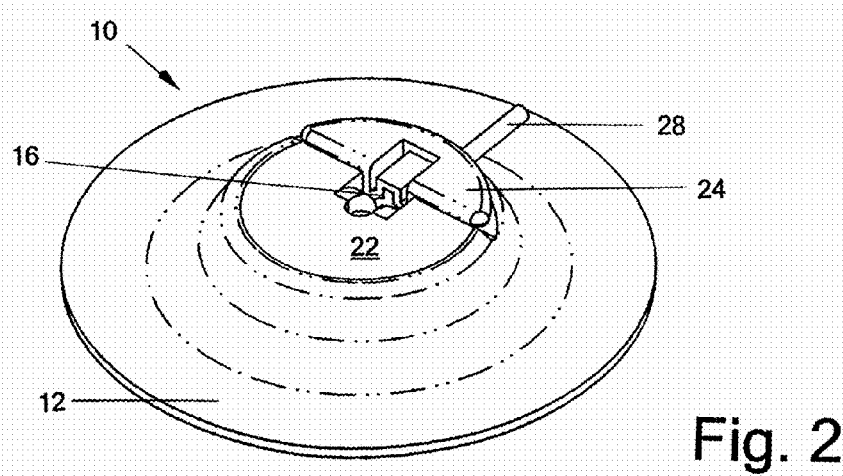
FIG. 2 illustrates a top perspective view of the present system with the connection unit attached to the infusion unit in the fluid delivery position.

FIG. 2 is a perspective view of an embodiment of the present system 10 with the emplacement member removed and the infusion fluid connection unit 24 removably attached to the main fluid infusion unit 11. The fluid delivery tube 28 is attached to provide for the flow of therapeutic fluid from the remote source to the patient.

Figure 2A:
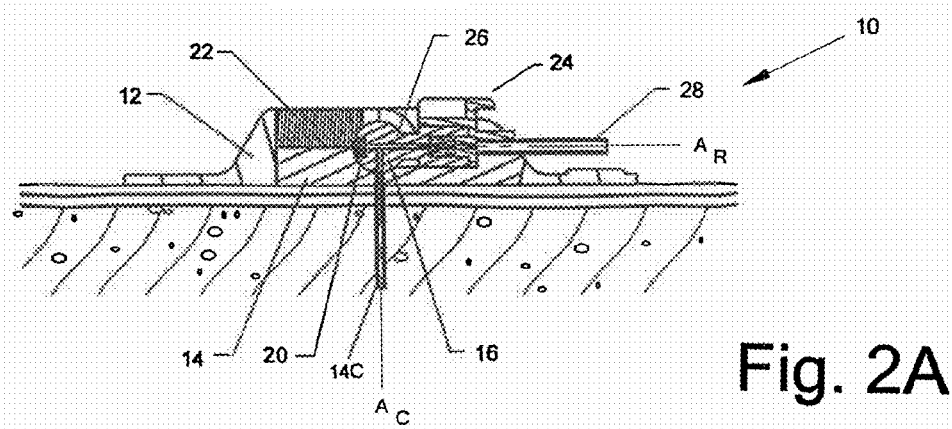
FIG. 2A shows a cross sectional side elevation view of one embodiment of the present system in the fluid delivery position.

FIG. 2A is a cross-sectional, side elevation view of the assembly 10 in a second delivery position. As may be seen in FIG. 2A, connection unit 24 has been attached to the rotating member 16 and rotating member 16 has been pivoted 90° to a second position. Thus, a comparison of FIGS. 1A and 2A discloses that the rotating member 16 is pivotable from a first position wherein the longitudinal arm axis $A_R$ is coincident or parallel and aligned with the longitudinal cannula axis, $A_C$ to a second position wherein the longitudinal arm axis, $A_R$, is perpendicular to the longitudinal cannula axis, $A_C$. As will be described below, when the connection unit 24 is attached to the rotating member 16 in this rotating member second position, the assembly 10 is positioned to deliver therapeutic fluid into the patient's body in what is called a delivery position.

Figure 3:
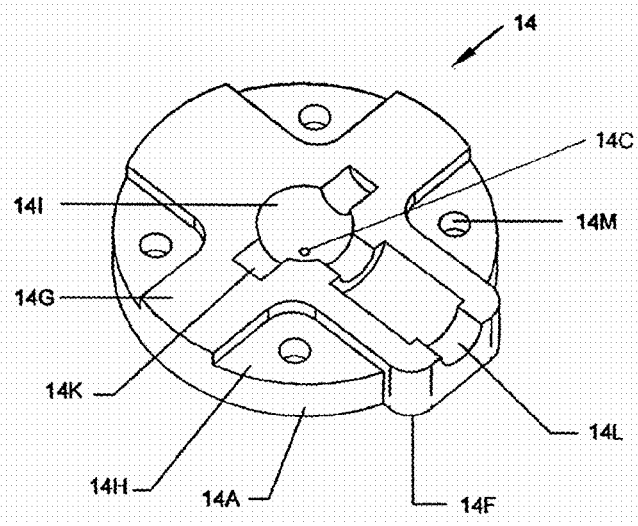
FIG. 3 illustrates a top side perspective view of one base of the present system.
Figure 3A:
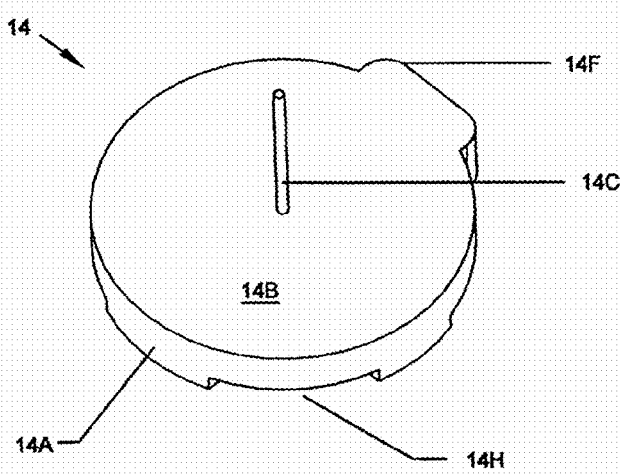
FIG. 3A shows a bottom side perspective view of the base of FIG. 3.
Figure 4:
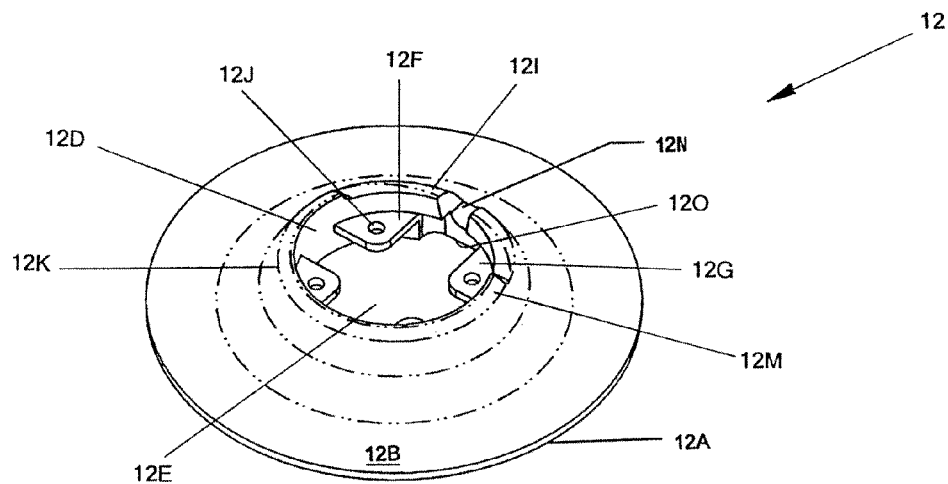
FIG. 4 is a top perspective view of a body section of the present system.

The rotation of member 16 from the first position to the second position ensures the accurate alignment of the fluid flow path from the source to the patient with little leakage. FIGS. 3 and 3A illustrate a base 14 whose function is to locate ball joint or rotating member 16 within main assembly body 12 and to provide engagement with the ball joint and to accommodate fluid communication between the ball and the vertically oriented cannula 14C, depending from a bottom surface 14B of the base. The base is also seen to have perimeter walls 14A describing a generally circular structure having a bottom surface 14B and a top surface 14G. Descending from the bottom surface 14B is the aforementioned cannula 14C which is attached to the base 14 near the center of the bottom surface 14B at a proximal end thereof, the cannula 14C being a cylindrical, hollow sheath structure having a distal end 14E having a conical cross section (see FIG. 3A). The function of the cannula 14C is to carry a fluid received from the ball joint 16 into the body of the patient. Thus, the base has a ball joint seat 14I in the top surface 14G thereof which corresponds to the outline of the ball joint 16. Cutouts 14H, located around the perimeter of top surface 14G, are provided to enclose legs (12F, 12G, 12H, and 12I) of base 12 (FIG. 4). Base 14 is also seen to include a boss 14F along the perimeter walls, the boss 14F for seating into notched-portion 12O of main assembly body 12. Apertures 14M are for receiving the receiving legs (22E, F, G, and H) of cover 22 (FIG. 6). Thus, it is seen that ball joint seat 14I is more particularly designed to receive ball joint 16, providing as part thereof ball joint engagement arm recess 14J for receipt of ball joint main body 16A thereinto, support on recesses 14K for receipt of support arms 16B therein (FIG. 5), and engagement arm recess 14L for receipt there into of engagement arm 16C of ball joint 16.

Figure 4A:
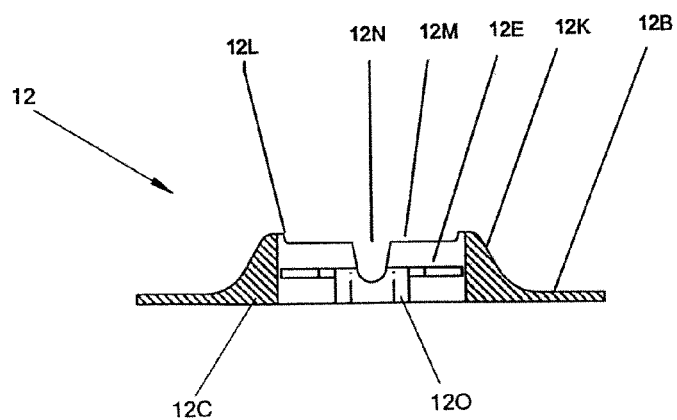
FIG. 4A shows a cross sectional view of a body section.

Turning now to FIGS. 4 and 4A, a main assembly body 12 is illustrated, the purpose of which is to provide a structure on which to locate the other assemblies of the fluid infusion unit 11, and to provide a bottom surface 12C attachable through an adhesive to the skin of a patient. FIG. 4A shows the main assembly body 12 as generally disc-shaped and having a low profile. The main assembly body 12 is typically approximately 0.8-inches in diameter with a height of about 0.29-inches. The novel design has achieved both a "low profile" (a height lower than approximately 0.30-inches) and a small "footprint" which has a radius of about 0.8-inches and a surface area of about 0.55 square inches. This provides what is generally described as a "small footprint." One embodiment of the invention provides a width-to-height ratio of approximately 2.75 to 1 (or lower).

The main assembly body 12 has a perimeter 12A and a top surface 12B, the top surface 12B including raised walls 12K, including walls 12D, defining a central opening 12E, into which is inserted from the under side thereof, the base 14. The main assembly body 12 includes legs (12F, G, H, and I) having apertures 12J therein, which legs receive cutouts 14H of the base when the base is inserted upwards through the bottom of the main assembly body 12 into central opening 12E with apertures 12J aligned with apertures 14M of the base, and with notched-portion 12O of main assembly body 12 for receipt of boss 14F of base 14. With base 14 properly inserted into central opening 12E from below main assembly body 12, cutouts 14H and legs (12F, G, H and I) will seat together and cannula 14C will be seen to project below main assembly body 12, as is best seen with reference to FIGS. 1 and 1A. Main assembly body 12 includes upper lip 12L and fluid connector cutout 12M for engaging the fluid connector cover 24A and also feed tube engagement cutout 12N. In this configuration, it can be seen that a pivoting or ball joint 16, as more specifically described in FIGS. 5 and 5A, can be placed in ball joint seat 14I of base 14, as more specifically set forth in FIG. 3.

Figure 5:
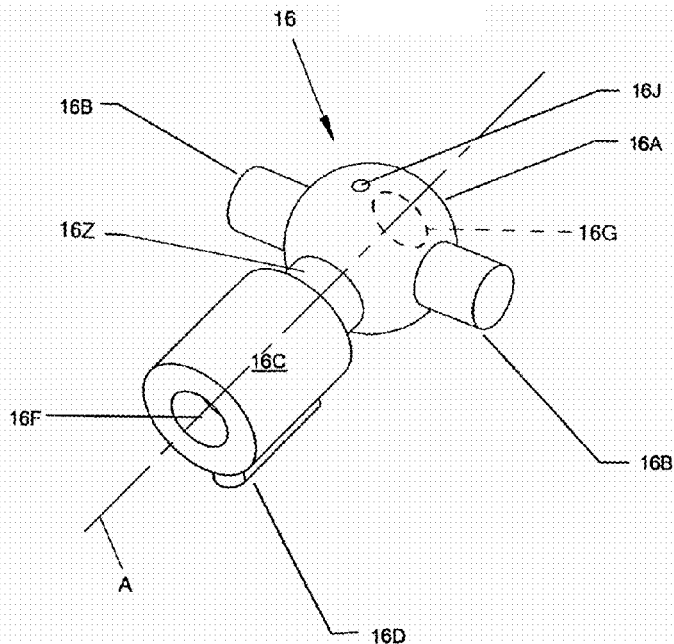
FIG. 5 is a perspective view of a rotating member of the present system.
Figure 5A:
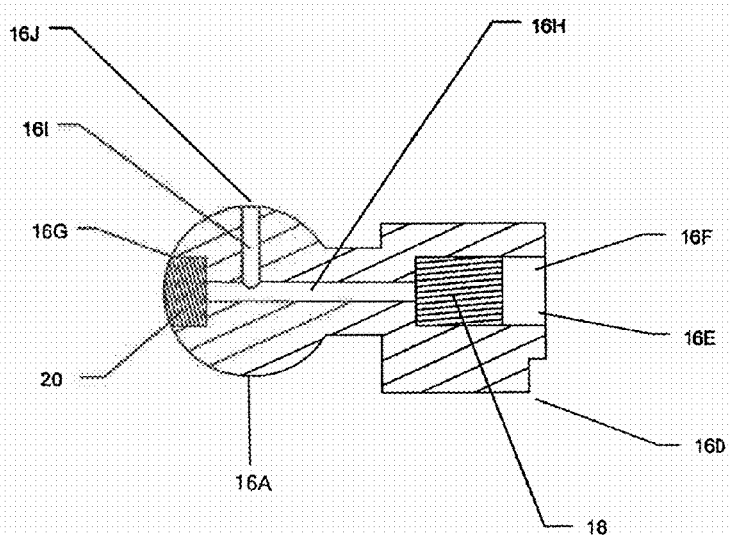
FIG. 5A is a cross sectional side elevation view of the rotating member of FIG. 5.
Figure 6:
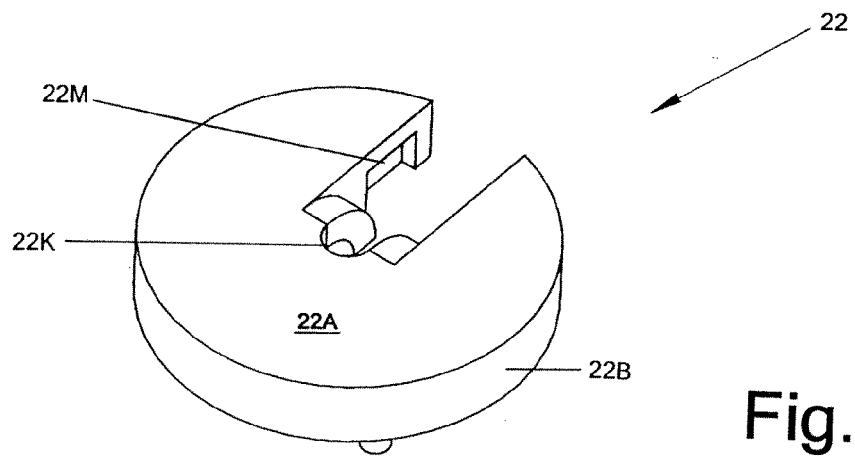
FIG. 6 shows a top perspective view of a cover of the present system
Figure 6A:
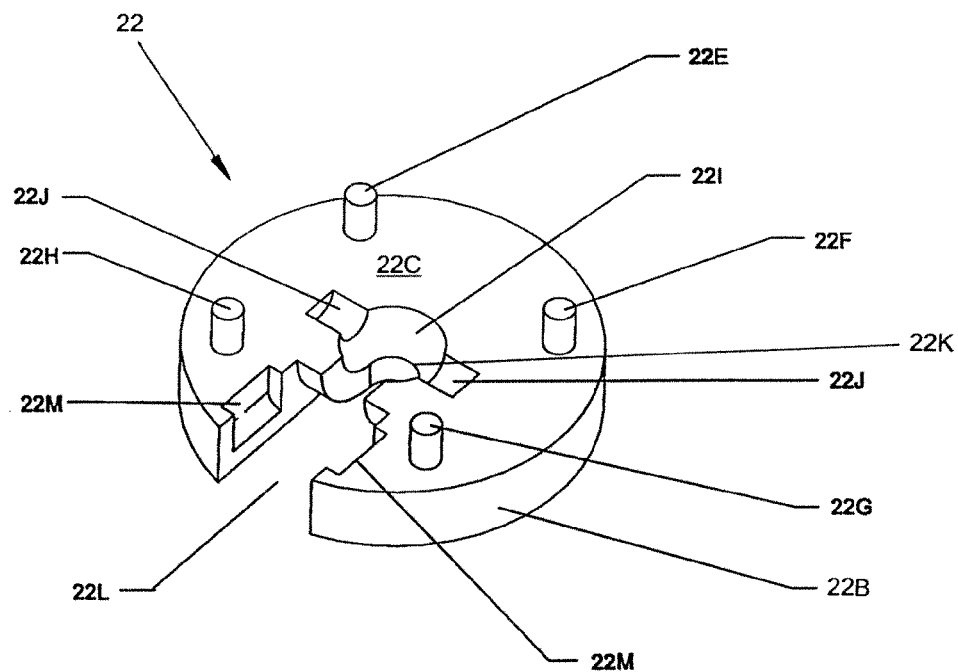
FIG. 6A illustrates a bottom perspective view of the cover of FIG. 6.

FIGS. 5 and 5A show the structure and components of the ball joint. Ball joint 16 typically includes at least partly a spherical main body 16A which is seen to have projecting therefrom cylindrical, opposed support arms 16B and, on an axis perpendicular to the axis described by the support arms 16B; this is seen to have an engagement arm 16C. Support arms 16B support the ball joint within support arm recesses 14K of the base 14 and also, within support arm cutouts 22J of cover 22 (FIG. 6A). Engagement arm 16C is also seen to have a ball joint guide member 16D on a portion thereof and a longitudinal arm axis $A_R$. This will be seen to provide engagement with both the plug 25 and when the plug 25 is removed, with the fluid connection unit 24 (see ball joint guide notch cutout 24D in FIG. 7).

FIG. 5A shows in cross section that the interior of ball joint 16 includes a central channel or bore 16E having an enlarged or cut out first end 16F and an enlarged or cut out second end 16G and a central portion 16H between the first end and the second end. Generally perpendicular to the central bore 16E and connected with the central portion 16H thereof is a feed channel bore 16I which communicates with the surface of the ball body of the rotating member 16 at aperture 16J. Further, it is seen that the first septum 18 seats recessed within enlarged or cut out first end 16F and second septum 20 seats snugly within enlarged second end 16G. There is a neck 16Z between ball joint main body 16A and engagement arm 16C.

FIGS. 6 and 6A illustrate details of the cover 22. FIG. 6 is a top side perspective view while FIG. 6A is a bottom side perspective view. The cover 22 is generally disc-shaped and designed to fit in the central opening 12E of the main assembly body 12, as seen in FIG. 1A, such that legs (22E, F, 7 G, and H) are insertable through apertures 12J in each of main assembly body legs (12F, G, H, and I) and further, such that legs (22E, F, G and H) extend through the main assembly body legs and into base 14 at apertures 14M in the base. Thus, legs (12F, G, H and I) of main body 12 and legs (22E, F, G and H) of cover 22 engage one another and base 14 to sandwich ball joint 16 within central opening 12E and between the base 14 and the cover 22.

FIG. 6 shows that cover 22 is generally disc-shaped and includes a top surface 22A and perimeter walls 22B, the perimeter walls 22B being designed to engage the walls 12D defining central opening 12E of body 12. Cover 22 is in FIG. 6A to have a lower surface 22C. Projecting from the lower surface 22C are the aforementioned cylindrical legs (22E, F, G and H) dimensioned to engage both the apertures 12J of the main assembly body 12 and apertures 14M of the base. Cover 22 is also seen to have defined on a lower surface thereof, a recessed portion or ball joint seat 22I, the ball joint seat 22I including recess for ball joint support arm cutouts 22J and ball joint engagement arm cutouts 22L. The lower surface 22C of the cover also includes a neck cutout 22K, for allowing the ball joint 16 to rest in an up position (see FIG. 1A), and a ball joint seat 22I where a ball joint 16 may rest. Moreover, it is seen that ball joint seat 22I is configured such that the ball joint 16 may be pivoted in a plane parallel to that of the cover surfaces 22A and 22B (a "down" position)(see FIG. 2A) and thus, rest with the engagement arm 16C of the ball joint 16 in ball joint engagement arm cutout 22L or, the ball joint 16 may be rotated to a position perpendicular thereto, as is illustrated in FIG. 1A, such that the engagement arm 16C rotates out of engagement arm cutout 22L and stands perpendicular to top surface 22A. Further yet, it is seen that cover 22 includes fluid connector locking boss coves 22M for lockingly maintaining the fluid connector in a down or "use" position as set forth in more detail below and with reference to FIG. 9.

Figure 7:
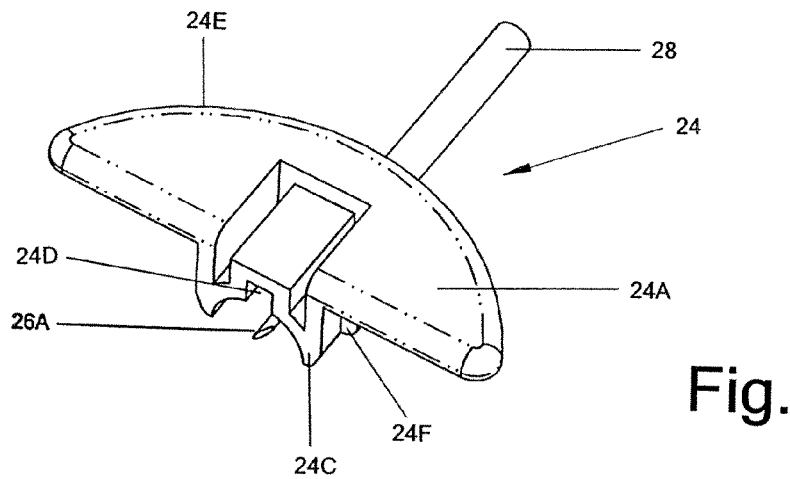
FIG. 7 is a top perspective view of a fluid infusion connection unit with a delivery tube attached.
Figure 7A:
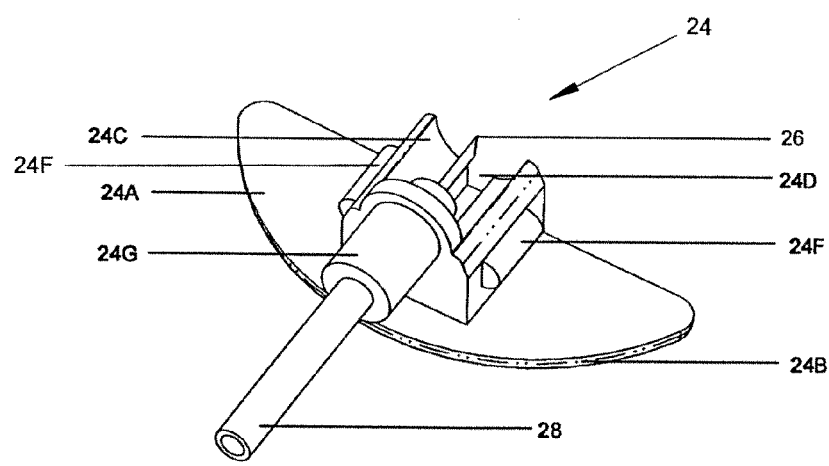
FIG. 7A is a bottom perspective view of the unit of FIG. 7.
Figure 7B:
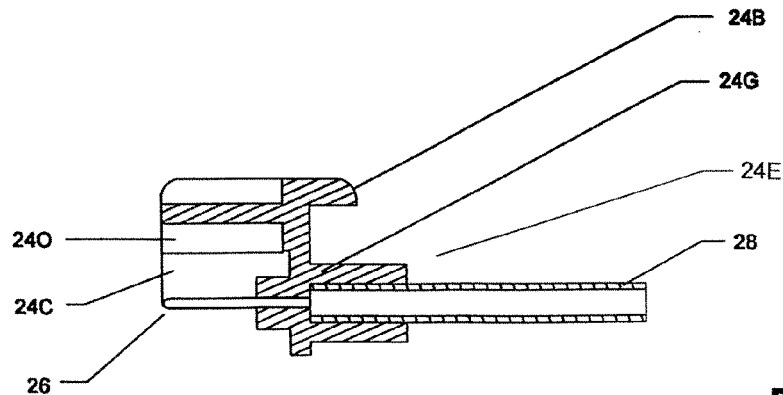
FIG. 7B is a cross sectional side elevation view of the unit of FIG. 7.

FIGS. 7, 7A and 7B illustrate the infusion fluid connection unit 24. The function of unit 24 is to provide a means for delivery of a fluid to the remaining elements of the infusion assembly 10 to ultimately reach the patient through the cannula 14C. The general method of doing so is to connect a feed tube 28 bearing a fluid therein to a needle 26 having a removed end 26A. The needle 26 will penetrate first septum 18 to deliver a fluid into the central bore 16E of the ball joint 16 for delivery through feed bore 16I to cannula 14C as set forth in FIG. 2A. Note that the first septum is "self sealing" such that when needle 26 is removed, for example, temporarily when a patient wishes to leave his or her bed, no fluid that has left the needle and is in the injection assembly will escape.

Fluid connection unit 24 has a semi-circular shape cover plate 24A defining a cover perimeter 24B. The cover cooperates with the flat shoulder 22A of the main body 12. Projecting from the cover 24A are walls defining a rotating member engagement portion 24C, these walls contiguous with a ball joint guide cutout 24D. When the fluid connection unit 24 is engaged to the ball joint so that needle 26 penetrates the first septum, engagement portion 24C will partially enclose the engagement arm 16C such that ball joint guide member 16D is seated snugly within ball joint guide cutout 24D. It is also seen in FIG. 7A that fluid connection unit 24 includes, on walls perpendicular to cover 24A, a pair of oppositely disposed locking bosses 24F for locking engagement with fluid connection boss coves 22M of cover 22 when fluid connection unit 24 is in a down or use position, as set forth in FIG. 9. There are a number of advantages to the fluid engagement means, which consists of a pair of locking bosses 24F releasably engaging fluid connection boss coves 22M. First, there is the tactile "feel" that the patient will get when the bosses "pop" into the coves. Second, there is the audible "click" that occurs when the bosses "pop" into the coves. Both of these sensory signals are important to assure the patient that the fluid connection unit 24 is locked onto the main infusion unit 11 and locked down to ensure communication with the cannula 14C, thus ensuring that the fluid flowing through the delivery tube is in fact flowing through the cannula 14C and into the patient. Such a releasable, positive lock down system helps prevent accidental dislodings of the tubing. Further, the system of a ball joint guide cutout 24D and ball joint guide member 16D provides for easy and effective alignment of fluid connection unit 24 to the engagement arm 16C of the ball joint 16 to easily and positively affix the infusion tubing to the assembly via a keyed mating of the tubing to the ball joint 16. The present system 10 removes the tubing from the main assembly body 12 and does not leave a "tail" of delivery tubing as is found in prior art systems which provide disconnect spliced into the delivery tube itself, rather than at the removed end.

Figure 9:
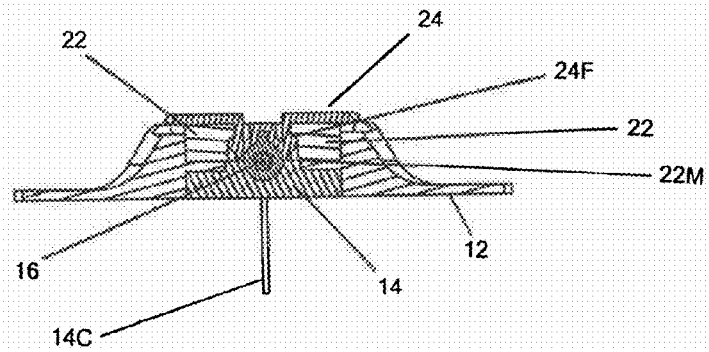
FIG. 9 is a cross sectional view of the system illustrated in FIG. 2.

It is seen with reference to FIGS. 7, 7A and 7B that fluid connection unit body 24E includes feed tube engagement collar 24G to receive the end of feed tube 28 and to provide a sealed mounting boss for needle 26. Thus, a function of fluid connection unit 24 is to provide means to receive the feed tube 28 in fluid tight relation and to mount needle 26 therein in a manner that will allow the needle 26 to align properly with the ball joint 16. Further, it allows the fluid connection unit 24 to move down and lock as it is joined to the ball joint 16 in a down, folded or use position, as seen in FIG. 9.

Figure 8:
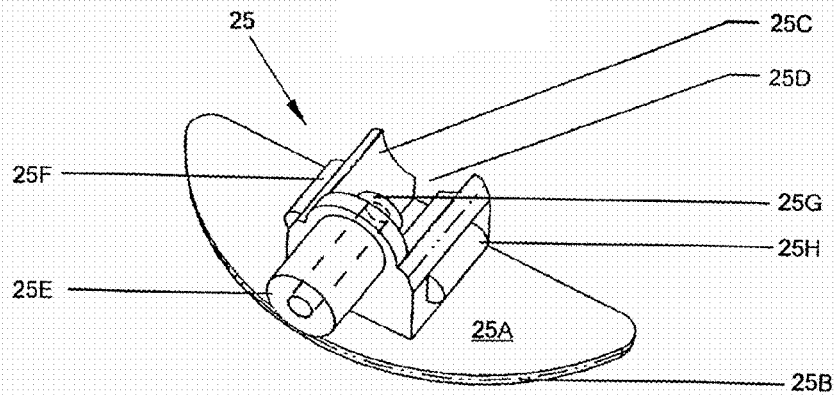
FIG. 8 is a bottom perspective view of a plug of the present system.
Figure 8A:
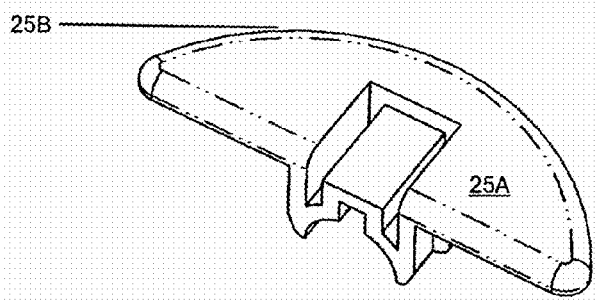
FIG. 8A is a top perspective view of the plug of FIG. 8.

Turning now to FIGS. 8 and 8A, details about the plug 25 may be appreciated. The functions of plug 25 are several. The first is to provide a means to effectively guide the emplacement member 30 and needle 32 through the two septums and into the cannula 14C when fluid infusion unit 11 is first engaged in the body of the patient, thereafter when the emplacement member 30 is removed from the infusion unit and discarded. A second function of the plug 25 is to provide a means to seal off the distal end of the engagement arm 16C when the fluid connection unit 24 is removed therefrom. It may be appreciated that plug 25 may fit snugly against the first septum 18 when the fluid connector is removed therefrom to keep dust and air from reaching that surface.

It is seen in FIGS. 8 and 8A that plug 25 includes a cover portion 25A defined by a cover perimeter 25B, the cover being semi-circular in shape, the shape of the plug 25 being substantially identical to the fluid connection cover plate 24A, both of these covers being dimensioned to fit within fluid connector cutout 12M of upper lip 12L of main body assembly (see FIGS. 4 and 4A). That is, when either the fluid connection unit 24 or plug 25 are connected to engagement arm 12C of ball joint 16 and ball joint 16 is in a folded or down position as is set forth in FIG. 2A, then either of the covers will fit snugly within cutout 12M of main assembly body 12 such that perimeter 24B or 26B, as the case may be, will be flush with upper lip 12L of main assembly body 12.

Plug 25 also includes an emplacement member plug portion 25E and needle guide portion 25G. As was seen in FIG. 1A, portion 25E will fit snugly within emplacement member 30 and needle guide portion 25G of plug 25 will fit snugly within first end 16F of central bore 16E of engagement arm 16.

FIG. 9 illustrates a cross sectional view of a first embodiment of the present invention with the fluid infusion connection unit attached and the assembly in the fluid delivery position.

Figure 9A:
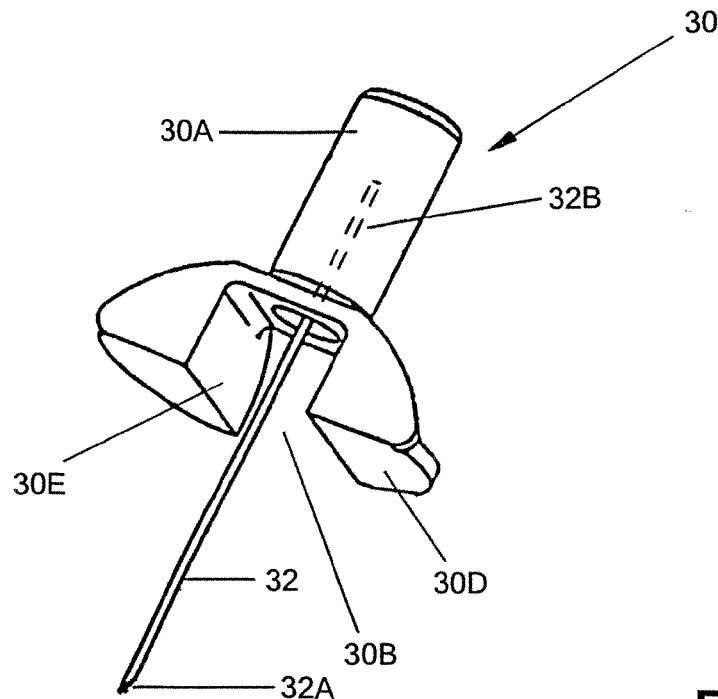
FIG. 9A is a first side perspective view of an emplacement member of the present system.
Figure 9B:
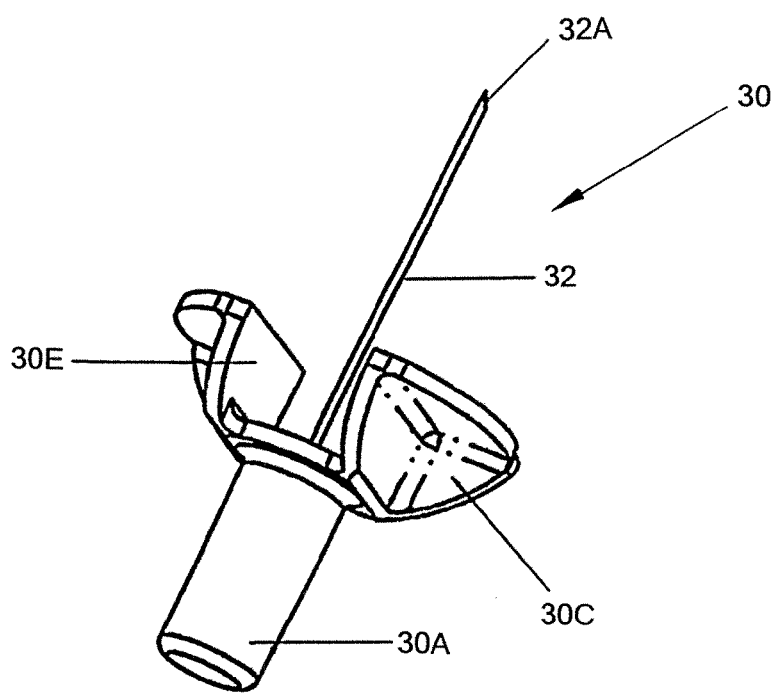
FIG. 9B is a second side perspective view of the emplacement member of FIG. 9A.

Emplacement member 30 is illustrated in FIGS. 9A and 9B. A function of member 30, as set forth earlier, is to provide a means through use of needle 32 having pointed end 32A for inserting the cannula 14C under the skin of the patient prior to commencement of delivery of the fluid thereinto. Thus, member 30 is seen to include a long, sharp needle 32 having a pointed distal end 32A and a proximal end 32B where it joins the head of the member. Member 30 further includes a cylindrical elongated grasping head 30A and walls defining a guide cutout 30B. The member also includes vertical walls 30C and, perpendicular thereto, a base 30D. Adjacent and removed from the grasping head are a pair of parallel side walls 30E. Side walls 30E engage the plug 25 as set forth in FIGS. 1A and 1B to seat needle 32 in plug opening 25H. Thus, the purpose of the member 30 is to cooperate with the plug 25 to maintain the needle 32 with elongated opening 25H which is itself aligned with the longitudinal axis of cannula 14C. When member 30 is inserted through the two septums its central longitudinal axis will be coincident with the longitudinal axis of cannula 14C. Further, the depth to which the member 30 is inserted is sufficient so the needle pointed end 32A projects just beyond the distal end of cannula 14C as seen in FIG. 1A. The cannula 14C is perpendicular to the lower surface of the infusion unit 11. This makes for efficient emplacement of the infusion unit onto the patient. When the delivery tube 28 is attached through the fluid connection unit 24 into the main body 12 of the fluid infusion unit 11, the tube 28 is perpendicular to the cannula 14C and almost flush with the skin. The present infusion assembly 10 is unique in providing a cannula projecting perpendicular into the surface of the skin while providing delivery tube that joins the assembly body perpendicular to the cannula and almost flush with the skin. This helps provide a "low profile" and a "snag free" assembly.

It should be noted that any or all parts of the invention may be made from anti-bacterial materials known in the trade. Further, the invention provides a fluid infusion assembly 10 with a ball joint 16 that is rotatable between a first position parallel to and coincident with the cannula 14C to a second perpendicular arrangement. In an alternate preferred embodiment, snaps, detents or other means to releasably retain the ball joint 16 in the perpendicular fluid delivery position, the parallel position and also a position half-way between the two, or at 45 degrees with respect to the perpendicular. This provides an additional position should the patient want to use the assembly without the ball joint 16 being either perpendicular or parallel.

Figure 10:
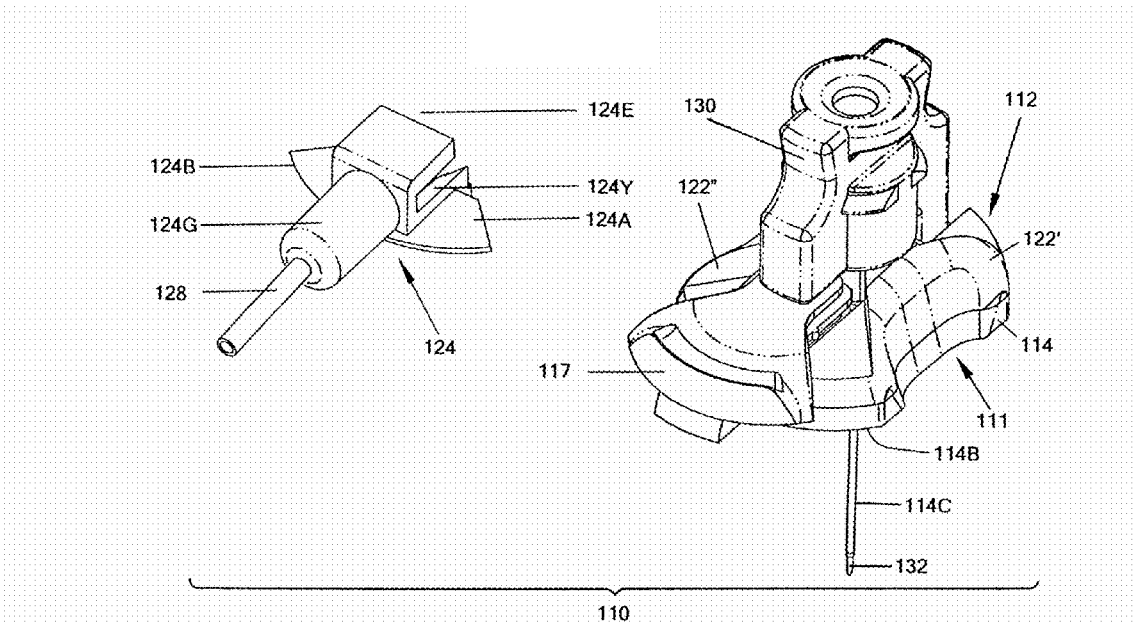
FIG. 10 is a perspective view of a second embodiment of the present system showing a second embodiment infusion unit with a second embodiment emplacement member attached and a second embodiment fluid infusion connection unit ready for attachment to the second infusion unit.

FIG. 10 shows an alternative infusion assembly 110 having a main infusion unit 111 and a fluid infusion connection unit 124. An emplacement member 130 is shown affixed to the body 112 of the unit 111 with cannula 114C projecting perpendicularly downward from the bottom surface 114B of base 114. As discussed above relating to another embodiment 10 of the invention, the insertion needle 132 extends beyond the distal end of the cannula. A two-piece cover 122' and 122" engages the base 114 and retains a rotating member 116 (FIG. 10A) within the main body 112.

Figure 10A:
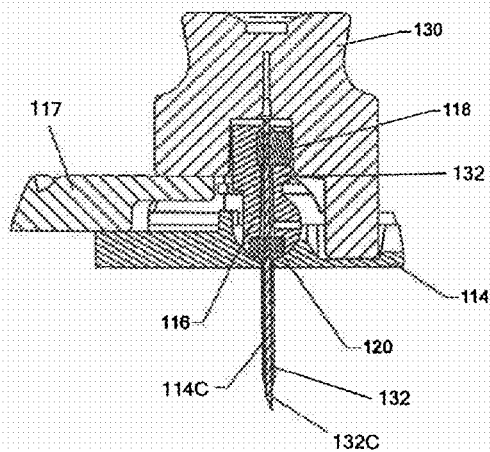
FIG. 10A illustrates a cross sectional view of a second embodiment of the infusion unit with the second embodiment emplacement member attached.
Figure 10B:
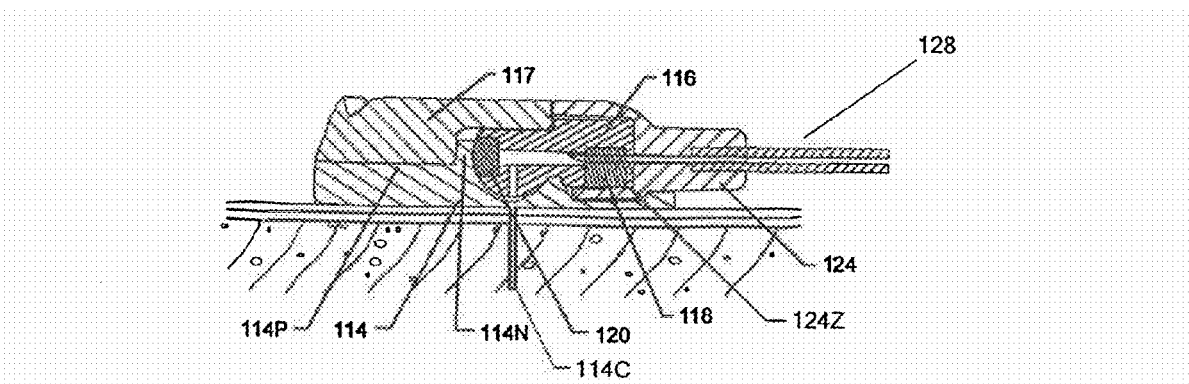
FIG. 10B is a cross sectional view of a second embodiment of the present system in the fluid delivery position.

The embodiment of FIG. 10 includes a lock 117 which will securely maintain the rotating member 116 in a "down" or locked position (FIG. 10B). FIGS. 10 and 10A illustrate the lock 117 in an unlocked, or disengaged position.

FIG. 10A for this embodiment 110 corresponds generally with FIG. 1A for the first embodiment 10. It should be understood that the same basic principals of operation are involved in these two embodiments. The fluid infusion unit 111 is attached to the patient by use of the emplacement member in cooperation with the cannula. Once the infusion unit is attached to the infusion site, the emplacement unit is discarded and the fluid connection unit 124 is attached to the rotating member 116. The rotating member is pivoted from a first position to a second position whereby therapeutic fluid from a remote source may be delivered subcutaneously to the patient's body. While the rotation of rotating member 116 ensures proper alignment of the fluid flow passages as was achieved with the first embodiment 10, the locking system 117 in this embodiment 110 results in a positive securing of the assembly in a fluid delivery position as shown in FIG. 10B.

Figure 10C:
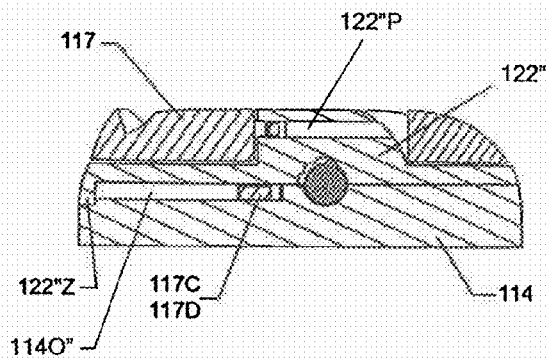
FIG. 10C shows cross sectional view of a second embodiment of the present system with a locking member for securing the rotating member.

FIG. 10A illustrates the infusion unit 111 with the emplacement member 130. Base 114 has perimeter walls 114A, bottom surface 114B, top surface 114G ball joint support arm recesses, pivoting joint body recess, engagement arm recess, apertures, and pivoting joint seat 114I in a manner as discussed with the first embodiment of unit 11. The function of the base 114 is the same as previously discussed. First, base 114 provides support for rotating or pivoting joint 116. Further, pivoting joint seat 114I and pivoting body recess provide support for rotating joint 116 whatever position the rotating joint 116 happens to be in. Furthermore, walls 114A of base 114 are configured to at least partially accept rotating joint 116 when it is in a down position. There are additional features to base 114 illustrated in FIGS. 10A and 10B that are not found in the first embodiment 14. For example, FIG. 10B shows that base 114 provides a lock stop 114N. Stop 114N acts as a stop against which lock 117 may rest. FIG. 10C shows base 114 has walls defining left channel 114O" which engage the lock 117 to the base 114. As the lock 117 slides in channel 114O" it will be prevented from backing out from the base by walls partially blocking these channels. Further, base 114 includes land 114P, also for accepting and guiding lock 117 between an "in" and an "out" position.

Figure 10D:
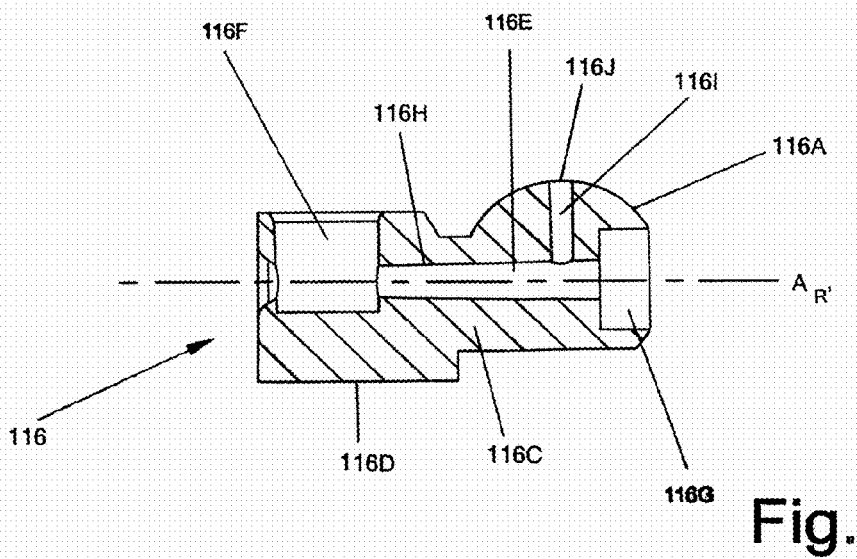
FIG. 10D is a cross sectional view of a second embodiment of a rotating member for the present system.

In the previous embodiment the functionally similar structure was sometimes referred to as a "ball joint" and is here being called a "pivoting" or "rotating" joint 116 in an effort to point out that while a "ball" shape, may, in part, provide for pivoting, in fact, the particular geometry of the structure is not crucial to its rotating nature. That is, rotating joint 116 is, similar to the ball joint 16, a rotating element which has channels within which will allow the insertion of an emplacement member through the joint when the joint is in a first position and, upon rotation will allow connection between a fluid infusion connection assembly and the cannula when it is in a second position, typically rotated any number of degrees, for example 90° from the first position. Ball joint or pivoting joint 116 is seen in FIG. 10D to have, typically, at least a partially spherical portion 116A and a pair of support arms (not shown). The support arms and at least part of the spherical portion 116A will rest in portions of base 114 as will be understood by reference to the figures. Engagement arm 116C will be seen to have central bore 116E and central portion 116H of central bore 116E aligned coincident with the longitudinal axis $A_R'$ of the engagement arm 116C. The axis of support arms is perpendicular to the axis of engagement arm 116C. Thus, the general design of the pivoting or rotating members of these embodiments includes two bores through the body of a pivoting member which are perpendicular to one another and to the axis of rotation, the two bores or channels for carrying fluid from a fluid connector to the cannula. Perpendicular to one of those two bores will be a central bore to carry the insertion needle for placement of the device on the skin of the patient.

As will be noted below there are embodiments of the present invention in which the rotating member does not have any bores or septums.

Ball joint or pivoting joint 116 is also seen to have guide member 116D which assists in engaging and guiding fluid connection unit 124 onto pivoting joint 116. Pivoting joint 116 and ball joint 16 both contain a similar arrangement of channels or bores throughout the body thereof. The purpose of these is twofold. First, a bore must be provided such that when the joint is in an up or vertical position a handle is engaged therewith, the handle having an insertion needle projecting downward through the cannula. The second function of the bores or channels in the body of the pivoting joint is for carrying fluid from the fluid connector to the cannula. The central bore 116E including central portion 116H will carry the needle of the handle when the device is placed on the patient. At least part of the central bore of pivoting member 116 will also provide for carrying fluid to the patient. However, pivoting member 116 provides, perpendicular to the central bore, a feed channel bore 116I which completes the necessary passageway to carry fluid from the fluid connection unit to the cannula (and into the patient) when the pivoting member or ball joint is in a down position. It is noted here that the pivoting or ball joint typically rotates about an axis perpendicular, and going through, the junction of the central bore and the feed channel bore.

Note with reference to FIG. 10D that pivoting joint 116 has a first cutout 116F and a second cutout 116G the first cutout 116F being at the first end and the second cutout 116G being at the second end, the two cutouts dimensioned for receipt of septums thereinto (see FIG. 10A). First cutout 116F brings the septum in from the side of the engagement arm instead of from the front engagement arm as set forth in the earlier embodiment. Ball joint or pivoting joint 116 also has an aperture 116J at the end of feed channel bore 116I for carrying fluid into the patient when the pivoting joint 116 is in a down position (see FIG. 10B).

Figure 11:
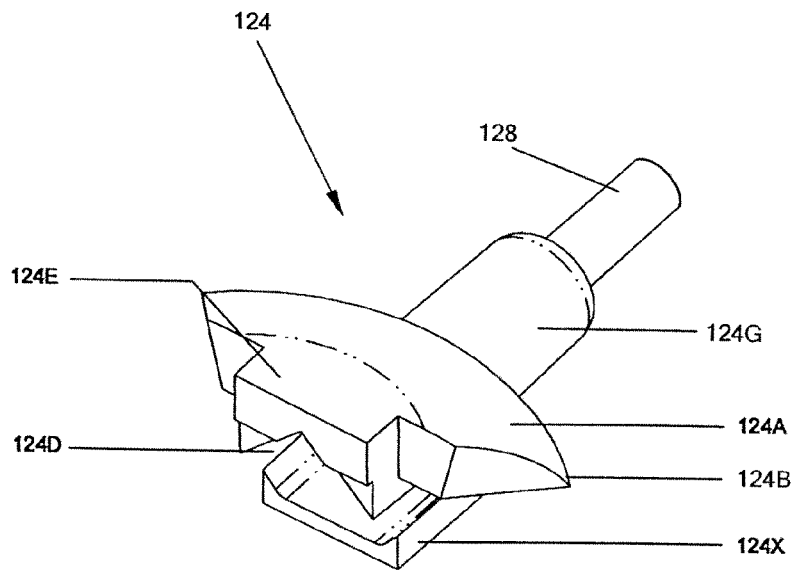
FIG. 11 is a top perspective view of a second embodiment fluid connection unit.
Figure 11A:
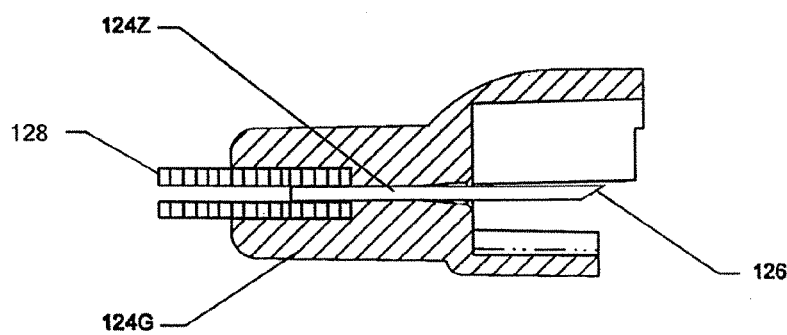
FIG. 11A is a cross sectional view of the unit of FIG. 11.

Turning now to fluid infusion connection unit 124, and FIGS. 11 and 11A, it is seen that unit 124 is designed to carry fluid into pivoting joint via a connection of a needle piercing the first septum 118 (see FIG. 10A). Fluid connection unit 124 includes a cover plate 124A having a cover perimeter 124B. The connector 124 also has a body portion 124E and extending from the body portion is a feed tube engagement collar 124G for engagement with a flexible feed tube 128. The feed tube will carry fluid and joins the needle 126 in feed tube engagement collar 124G. It is seen that needle 126 is held in body channel 124Z such that the feed tube engages the needle 126. Body portion 124E contains slots which slots will engage the outer edges of engagement arms 116C. Note that "V" shaped pivoting joint guide notch cutout 124D will guide "V" shaped fluid connection unit onto a "V" shaped engagement arm 116 of the pivoting joint while aligning needle 126 with the first septum of the pivoting joint and the central bore. Moreover, body 124E includes land 124X that will seat within of the engagement arm recess of base 114 when the connector is pushed onto the engagement arm and then the engagement arm is rotated to a down position (see FIG. 10B). Fluid connection unit 124 is typically urged onto the engagement arm when the engagement arm is in a 45° or a vertical position (FIG. 10A) until it is flush and then the joint is rotated to a down or 0° position (see FIG. 10B). This rotation of the coupled unit 124 and ball joint 116 should be done with the lock 117 in an "out" or disengaged position. When the coupled fluid connection joint engagement arm unit is rotated down, lock 117 can be slid forward until it is fully engaged against stop 114N and nose 117A overlies at least a portion of the rotating unit 116. When the lock 117 is moved forward it will hold down the pivoting joint 116.

Figure 12:
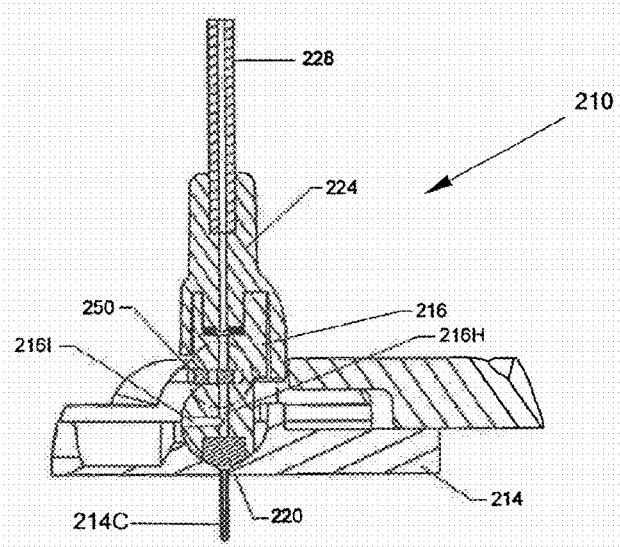
FIG. 12 is a cross sectional side elevation view of a third embodiment of the present system showing a third embodiment emplacement member attached to a third embodiment infusion unit.
Figure 12A:
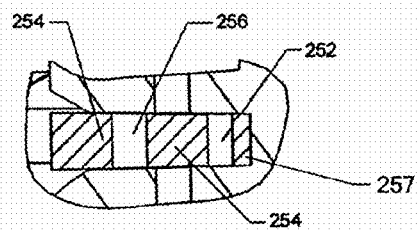
FIG. 12A shows a cross sectional view of a third embodiment in a fluid delivery position.
Figure 12B:
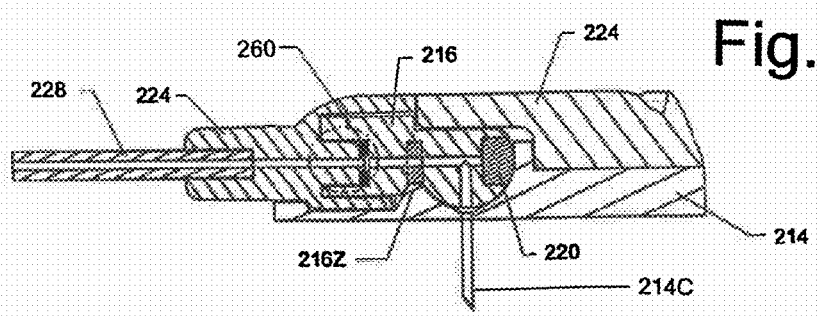
FIG. 12B is a partial cross sectional view of one position of the valving of a third embodiment of the present system.

FIGS. 12, 12A and 12B illustrate another alternate preferred embodiment of a fluid infusion assembly 210 which includes a rotating joint 216 which contains a slide valve 250 which slides back and forth in a slide valve chamber 252. The slide valve 250 includes a valve body 254 which includes walls defining a channel 256. The valve body 254 is designed to snugly fit adjacent the walls defining slide valve chamber 252. Slide valve 250 may slide back and forth in slide valve chamber 252 on a "living" hinge 257. In an "out" position as illustrated in FIG. 12, the slide valve body urged by hinge 257 blocks the channel of central portion 216H of central bore of joint 216. This is the position of the slide valve when fluid connection unit 224 is engaged therewith but rotating joint 216 in an "up" position, or, in fact, in any position but down. Note however that when fluid connection unit 224 is rotated to a down position such as illustrated in FIG. 12B, then interference with walls 216Z of base 214 causes slide valve 250 to move into a position such that channel 256 of slide valve 250 is aligned with central bore and liquid can pass through ball joint 216 and into the patient through the cannula 214C extending downward from the base 214. The use of the slide valve makes the first septum of the previous embodiments unnecessary, and therefore a needle on fluid connector 224 is, likewise, unnecessary. Instead, the embodiments set forth in this set of drawings uses gaskets where the channel of the fluid connection unit meets the rotating joint. The gaskets help provide a fluid tight fit with the fluid connector 224 to the ball joint 216 when the ball joint and fluid connector are engaged.

Figure 13:
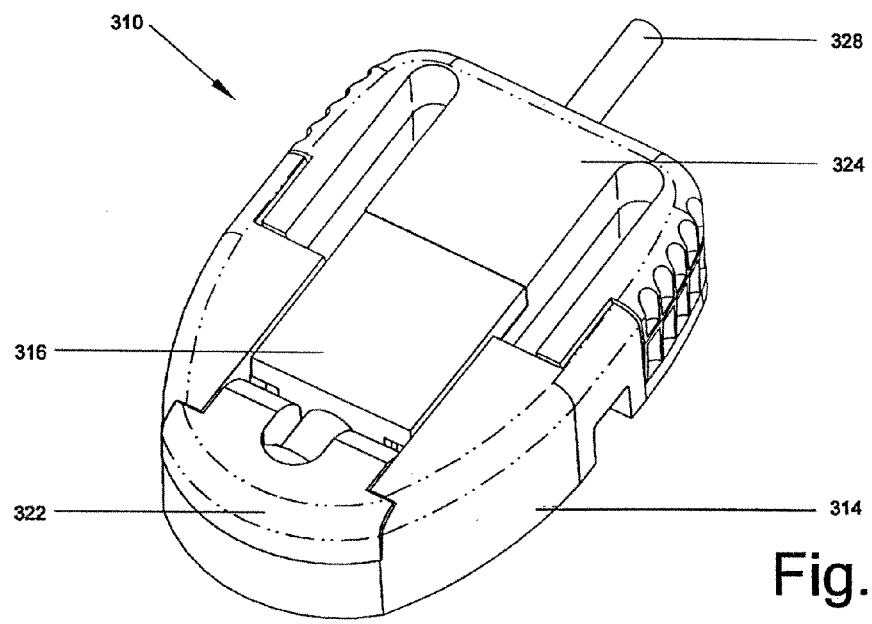
FIG. 13 is a top perspective view of a fourth embodiment of the present system in the fluid delivery position.
Figure 13A:
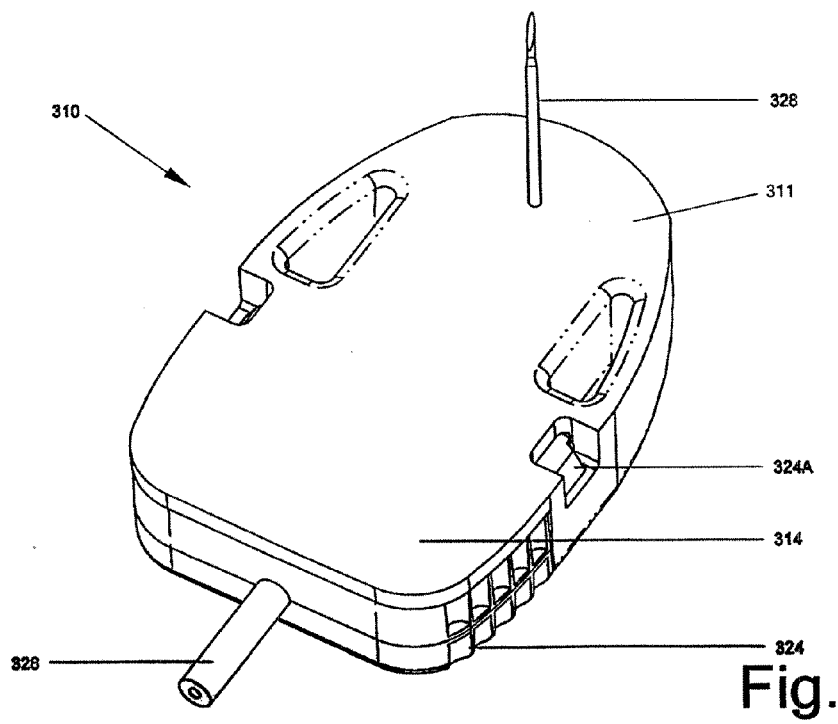
FIG. 13A is a bottom perspective view of the embodiment of FIG. 13.
Figure 13B:
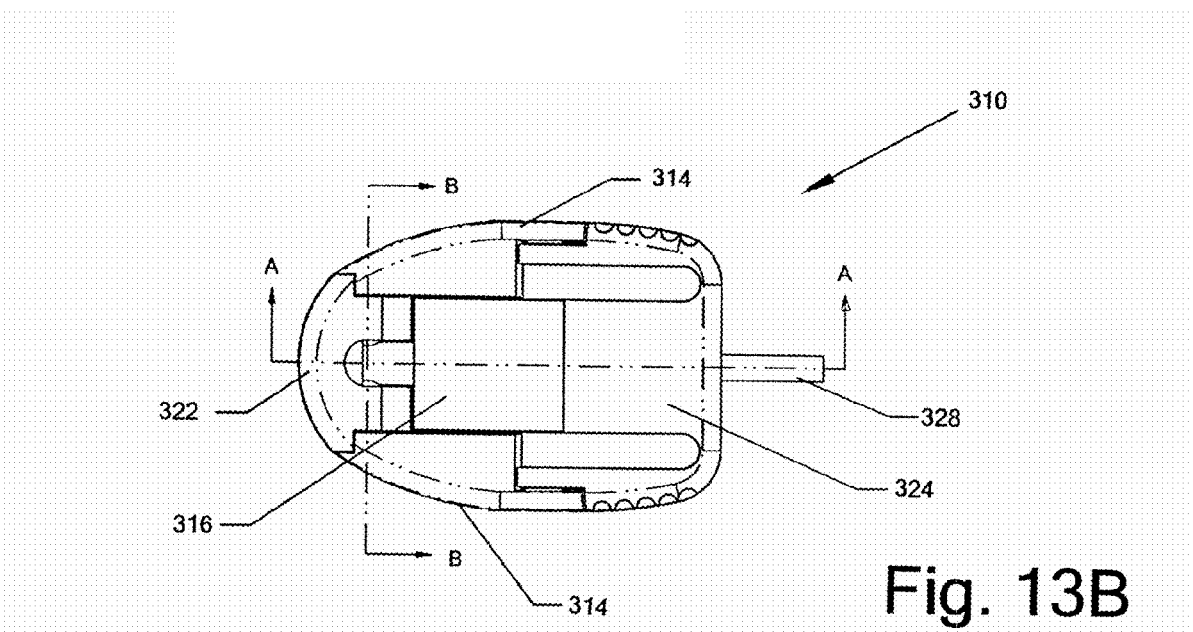
FIG. 13B is a top plan view of the embodiment of FIG. 13.
Figure 13C:
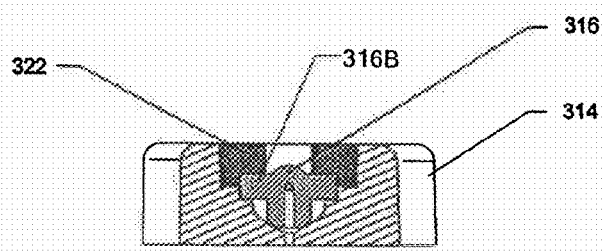
FIG. 13C is a cross sectional view taken along line B-B of FIG. 13B.
Figure 13D:
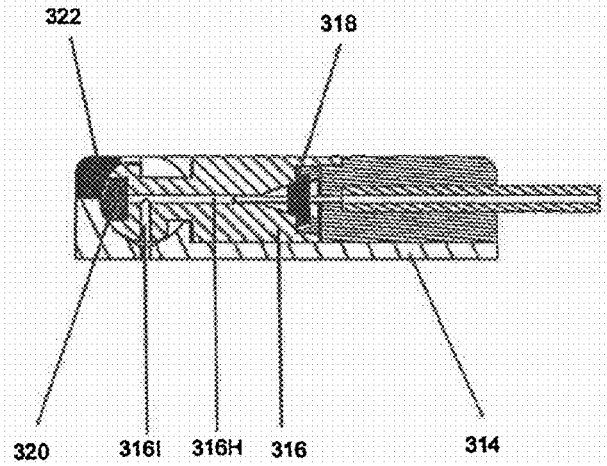
FIG. 13D is a cross sectional view taken along line A-A of FIG. 13B.
Figure 13E:
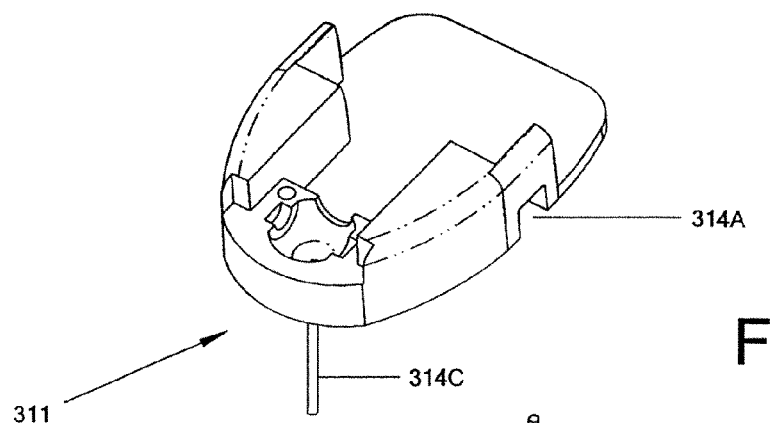
FIG. 13E is a top perspective view of a fourth embodiment of the infusion unit of the present system.
Figure 13F:
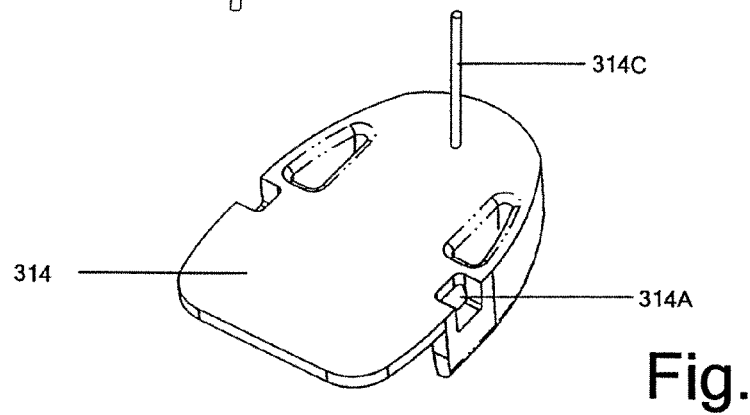
FIG. 13F is a bottom perspective view of the embodiment of FIG. 13E.
Figure 13G:
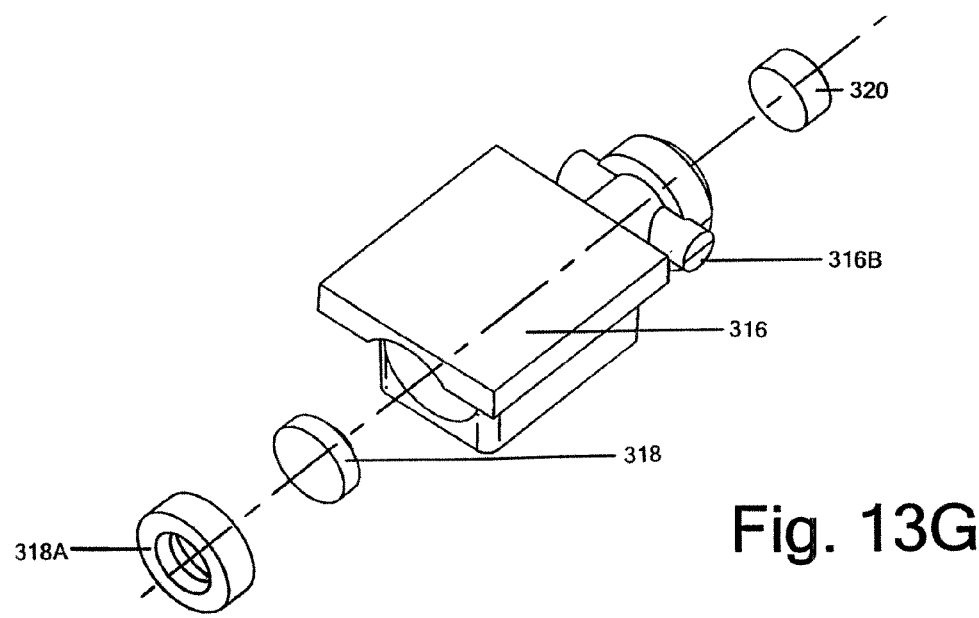
FIG. 13G shows an exploded top perspective view of a fourth embodiment rotating member.
Figure 13H:
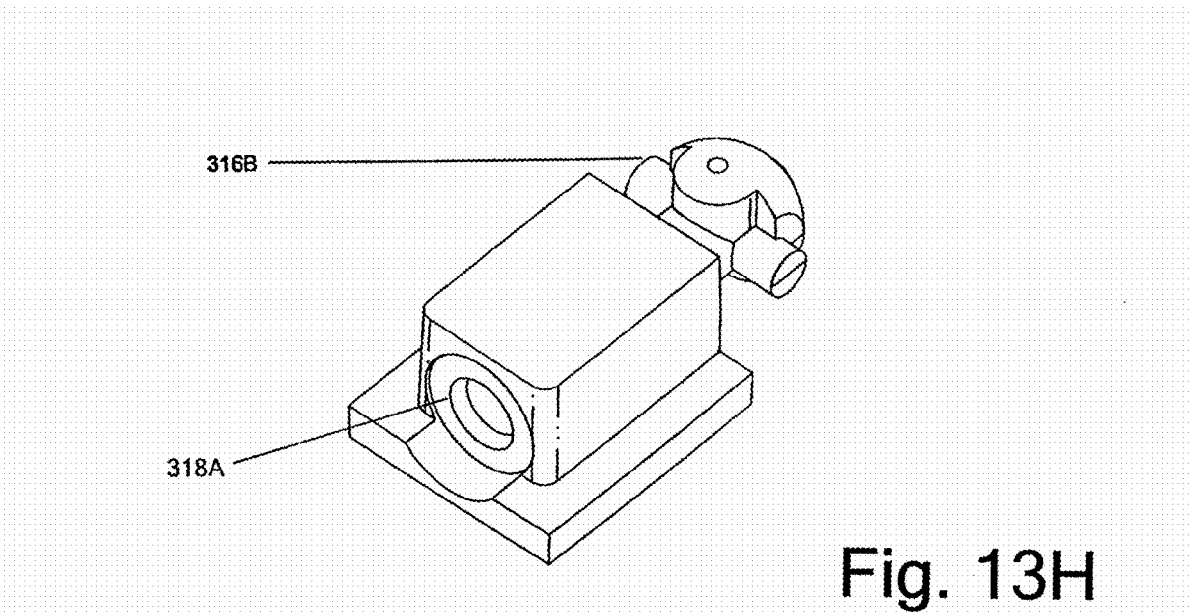
FIG. 13H illustrates a bottom perspective view of a fourth rotating member embodiment.
Figure 13I:
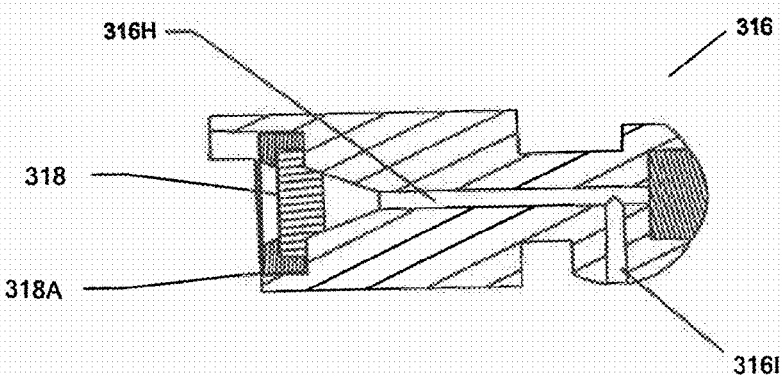
FIG. 13I illustrates a cross sectional view of the rotating member of FIG. 13H.
Figure 13J:
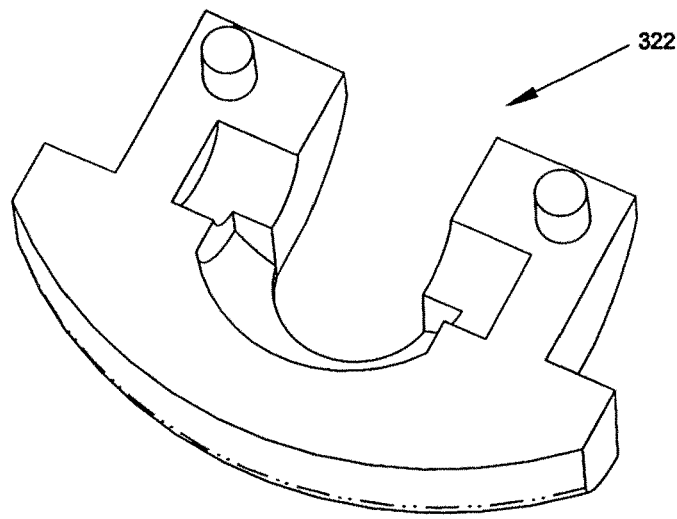
FIG. 13J is a bottom perspective view of a fourth embodiment cover of the present system.
Figure 13K:
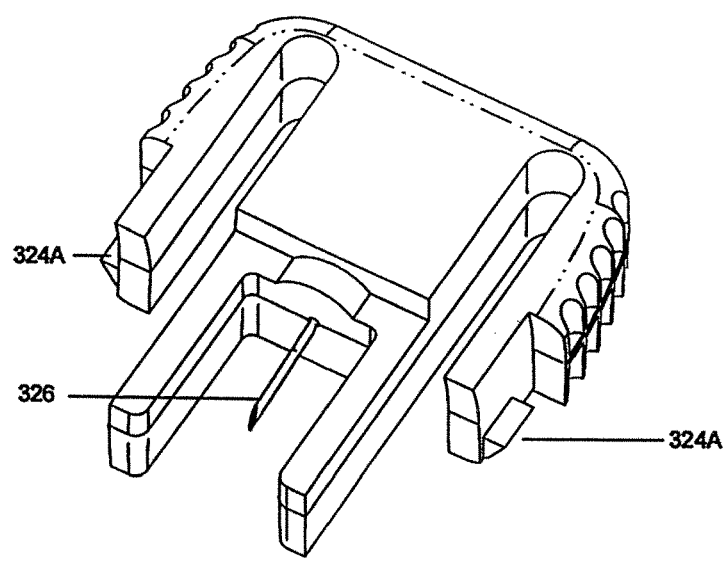
FIG. 13K shows a top perspective view of a fourth embodiment fluid connection unit.

Yet another embodiment of the present fluid infusion assembly 310 featuring a unique pivoting joint concept is illustrated in FIGS. 13 through 13K. In these figures the assembly is shown with the connection unit 324 attached to the infusion unit 311 in the second fluid delivery position. It should be understood that initially the infusion unit must be inserted in and attached to the patient's body as described with the previous embodiments. With the details of the earlier embodiments understood, this embodiment is seen to provide a one piece base 314 at least partially cut out to receive part of a pivoting joint 316 (see FIGS. 13D and 13E). Pivoting joint 316 lays in base 314 and is partially engaged with a one piece cover 322 for engaging support arms 316B. Note in FIG. 13K that connection unit 324 includes arms 324A that will engage slots 314A of base 314 (see FIGS. 13E and 13F) and also includes needle 326 and feed tube 328. As seen in FIG. 13D, pivoting joint 316 is seen to have a first septum 318 and second septum 320. The first septum is held in place in the rotating joint by means of a cap 318A. In FIG. 13I the two channels or bores 316H and 316I within the rotating joint may be seen, the bores are functionally equivalent to those seen in earlier rotating joints. In FIG. 13J, cover 322 can be seen with cutouts for at least partially enclosing the pivoting joint and legs for engaging the base.

Figure 14:
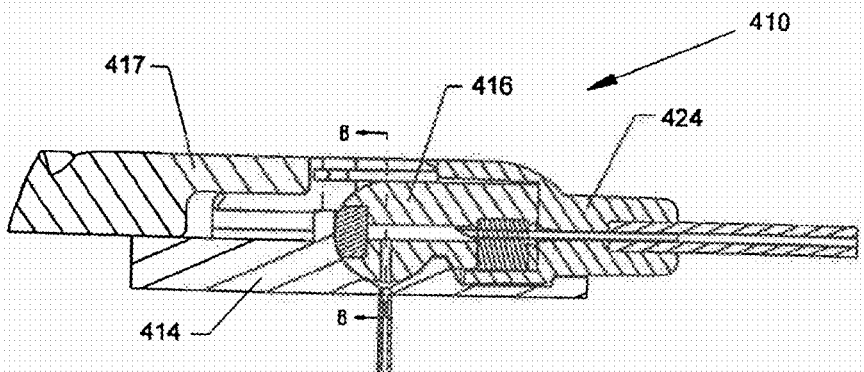
FIG. 14 illustrates in cross section a fifth embodiment of an infusion system of the present invention in the fluid delivery position.
Figure 14A:
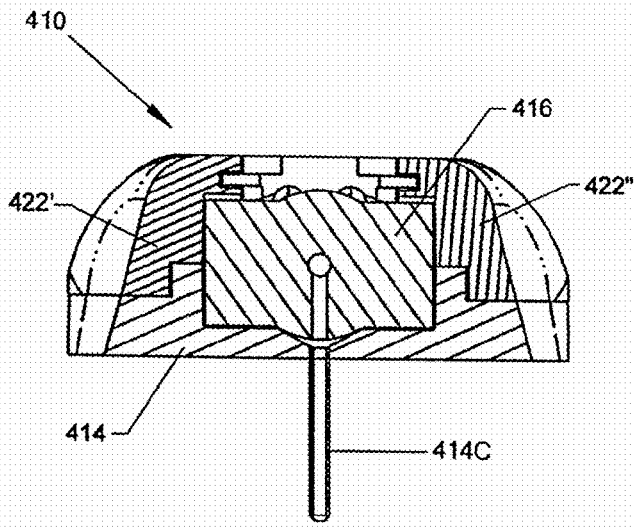
FIG. 14A shows in cross section a fifth embodiment with a "T" shaped rotating member.
Figure 14B:
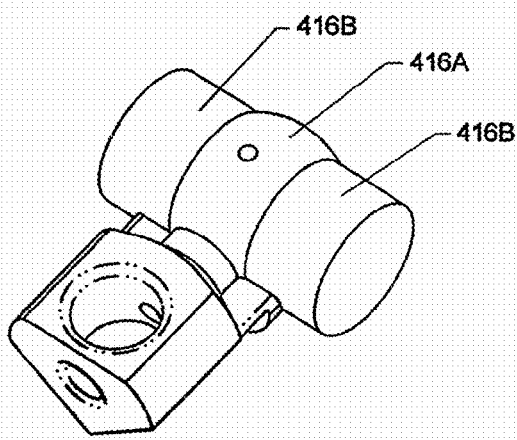
FIG. 14B is a perspective view of a "T" shaped rotating member of the present system.

FIGS. 14, 14A and 14B illustrate yet another alternative preferred embodiment of the present fluid infusion assembly 410 having a "T" shaped rotating joint 416. Here it is seen that alternate preferred embodiment of fluid injection assembly 410 has a base 414 and a pair of covers 422' and 422" which together will enclose a cylindrical portion 416A and cylindrical support legs 416B of the "T" joint in a manner that will allow the "T" joint 416 to pivot from a down position where fluid can be carried through fluid connector 424 into "T" joint 416 and down through cannula 414C into the patient. In an up or vertical position (not shown) a handle may engage the unit to insert the fluid injection assembly onto the patient. This alternate preferred embodiment also features a lock mechanism 417.

In some circumstances, it is desired to not have a fluid flow path through the rotating member, but rather to utilize the rotating member principally for its ability to properly align the fluid infusion connection unit with the infusion unit attached to the patient's body. Thus, yet another embodiment 510 of the present invention is illustrated in FIGS. 15 through 15D.

Figure 15:
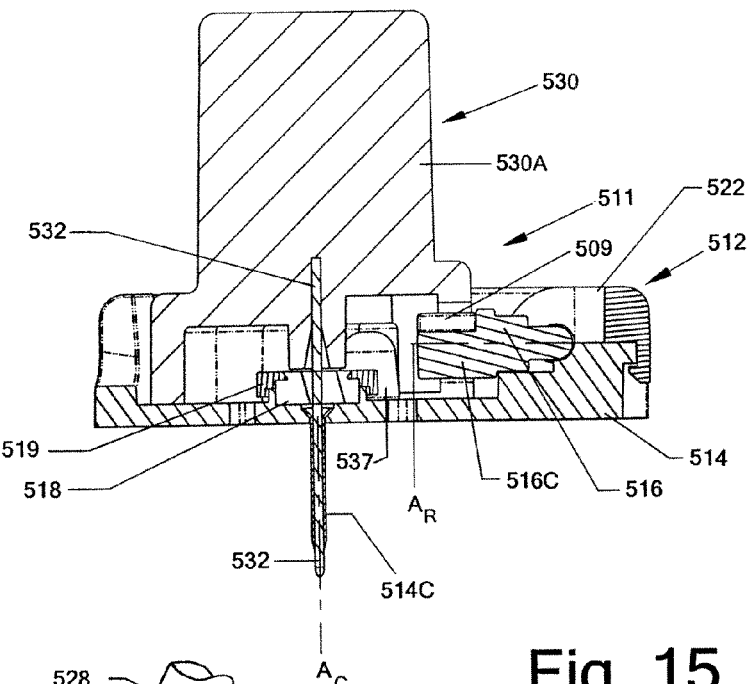
FIG. 15 shows a cross sectional side elevation view of a sixth embodiment of an infusion unit with an emplacement member attached.

With an understanding of the previous embodiments, it will be seen that FIG. 15 is a cross sectional, side elevation view of another embodiment of the infusion unit 511 with an emplacement member 530 attached thereto. The needle 532 of the emplacement member 530 is affixed to head 530A and passes through septum 518 attached to base 514 by septum locking cap 519. The needle 532 then passes through cannula 514C and extends beyond the distal end of the cannula. The use of a separate septum 518 with a locking cap 519 considerably reduces manufacturing costs and ensures flexible, pliable septum.

It should be noted that the rotating member 516 is sandwiched between cover 522 and base 514, as has been discussed with previous embodiments. However, in this embodiment 511, the rotating member 516 is in an initial down storage position without the fluid connection unit 524 attached. The engagement arm 516C has a longitudinal axis, $A_R$, which in this initial storage position is perpendicular to the longitudinal cannula axis, $A_C$, as seen in FIG. 15.

Figure 15A:
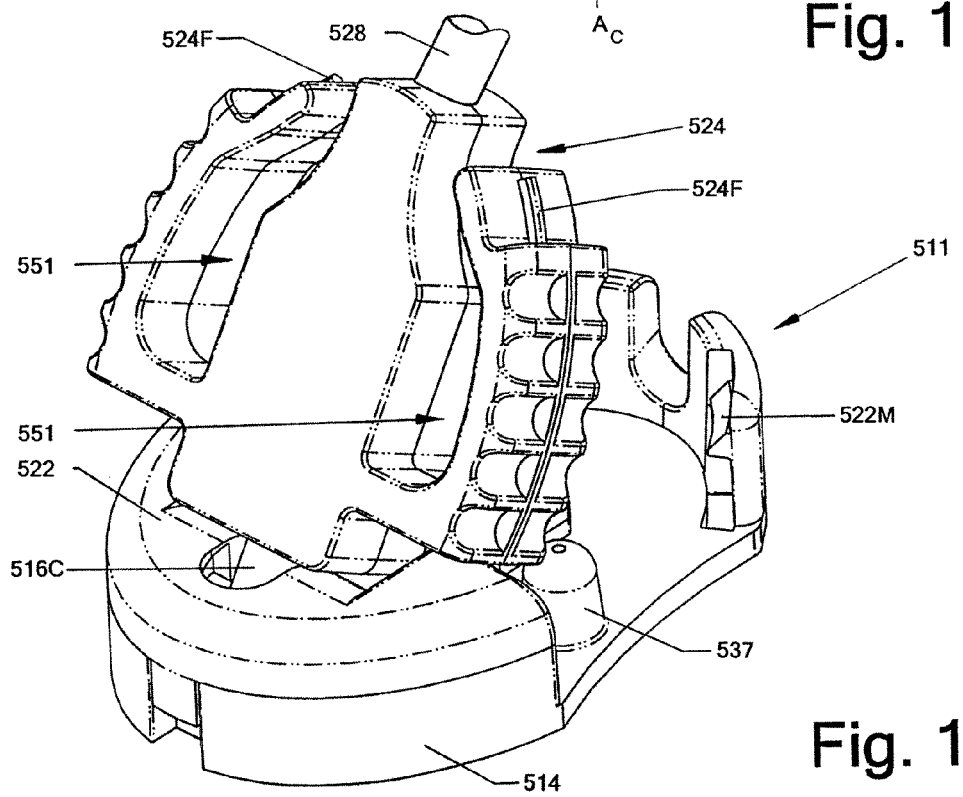
FIG. 15A is a top perspective view of a sixth embodiment of the present system in a partially rotated position.
Figure 15B:
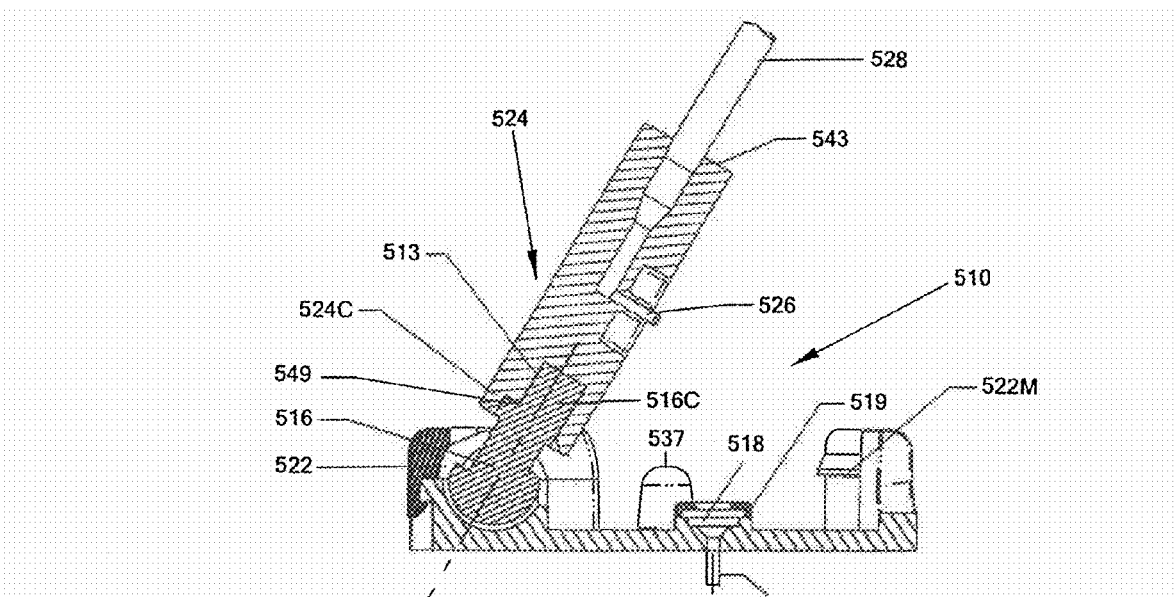
FIG. 15B is a cross sectional side view of the embodiment of FIG. 15A.

FIGS. 15A and 15B show the assembly 510 with the emplacement member 530 discarded and the fluid infusion connection unit 524 attached to the rotating member 516. The connection unit 524 has been slightly rotated from a first position where the longitudinal arm axis $A_R$ of the rotating member attachment arm 516C was parallel to the longitudinal cannula axis, $A_C$. In this first position the connection unit 524 is easily attached to the rotating member 516 by aligning the connection unit alignment key 513 with the engagement arm key way 509 (FIG. 15) and urging unit 524 until the engagement portion 524C is stopped against shoulder 549 of the rotating member 516. This ensures positive, accurate alignment of the connection unit 524 with the infusion unit 511 when rotation to the fluid delivery position is completed. Further, alignment accuracy is ensured by the cooperation of the alignment hubs 537 (one on each side of the infusion unit 511) with the connection unit arm openings 551 (FIG. 15A). As the connection unit 524 is rotated downwardly towards a second "down" position of the rotating member, the hubs 537 pass through the arm openings 551 to guide the connection unit 524 into the fluid delivery position.

The connection unit 524 is shown in FIG. 15B with a fluid delivery tube 528 attached to a first end 543 and a rotating member engagement portion 524C on an opposite end. A needle 526 extends from the underside of the connection unit 524. When alignment is proper, needle 526 will penetrate septum 518 allowing therapeutic fluid to flow to the patient.

FIG. 15A also illustrates the tactile "feel" mechanism of this embodiment 510. A pair of locking bosses 524F are releasably engagable with boss coves 522M when the connection unit 524 is "snapped" into a properly aligned fluid delivery position.

Figure 15C:
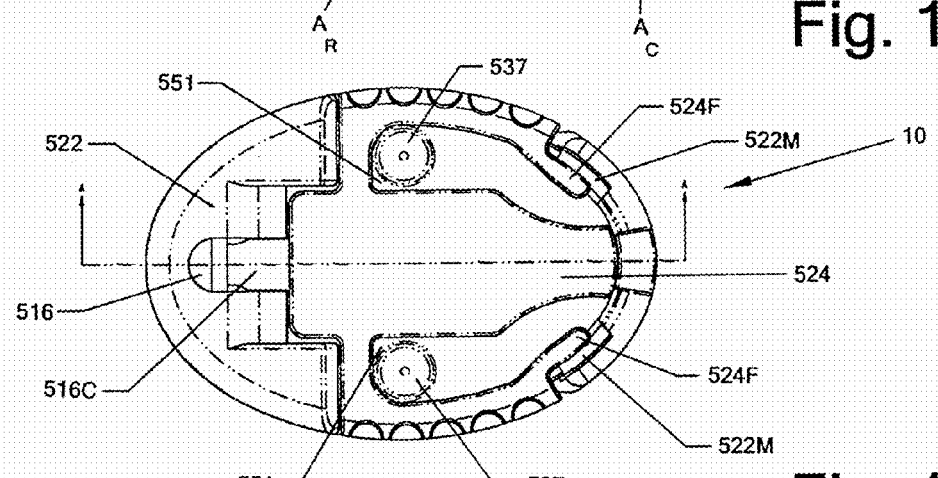
FIG. 15C is a top plan view of a sixth embodiment in the fluid delivery position.
Figure 15D:
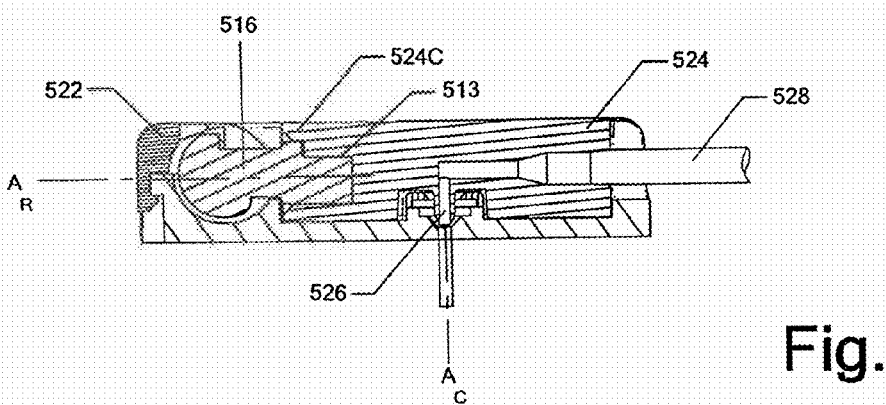
FIG. 15D is a cross sectional view taken along line A-A of FIG. 15C.

A top plan view of this embodiment 510 in the fluid delivery position is shown in FIG. 15C. The alignment hubs 537 are properly positioned with arm openings 551, and the locking bosses 524F are snapped into coves 522M. FIG. 15D is a cross sectional side elevation view of FIG. 15C taken along line A-A. As may be seen, the longitudinal arm axis, $A_R$, is perpendicular to longitudinal cannula axis, $A_C$. The needle 526 has penetrated septum 518 to allow fluid to be delivered through tube 528 to the patient.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

The invention claimed is:

1. A system for subcutaneous delivery of a therapeutic fluid from a remote vessel into the body of a patient, the system comprising:
a generally tabular assembly having a generally straight elongated cannula extending from a generally flat bottom surface;
a rotatable joint for engagement with the generally tabular assembly, the rotatable joint having an elongated engagement arm, the elongated engagement arm having a near end and a removed end and a joint body engaged with and integral with the near end of the elongated engagement arm having an axial aligned first fluid channel therethrough, the first fluid channel extending at least partially through the joint body;
the rotatable joint further having a second interconnecting fluid channel for intersecting with the first axially aligned fluid channel and with a surface of the joint body forming a fluid port thereby;
wherein the generally tabular assembly is adapted to engage the rotatable joint so as to provide rotation of the elongated engagement arm in a plane, the plane including the cannula of the generally tabular assembly;
wherein the elongated engagement arm is moveable between a first position, generally vertical to the generally tabular assembly, wherein the axially aligned first fluid channel is along an axis defining the cannula, to a second position, approximately perpendicular to the first position, wherein the second interconnecting fluid channel is in fluid communication with the cannula.

2. The system of claim 1, wherein the rotatable joint includes a valve for controlling the flow of therapeutic fluid through the fluid flow channels therein.

3. The system of claim 2, wherein the valve of the rotatable joint is adapted to open, so as to allow the flow of fluid therethrough, when the rotatable joint is in the second position.

4. The system of claim 1, wherein the generally tabular assembly includes a one piece base and a one piece cover, the base and cover cooperating to engage the rotatable joint to allow rotation thereof.

5. The system of claim 1, wherein the rotating joint is T-shaped.

6. The system of claim 5, further including a fluid connector removably engageable with the elongated engagement arm and engageable with a remote source of therapeutic fluid, wherein the fluid connector is adapted to releasably engage the elongated engagement arm, when the elongated engagement arm is out of the second position.

7. The system of claim 1, further including a fluid connector removably engageable with the elongated engagement arm and engageable with a remote source of therapeutic fluid, wherein the fluid connector is adapted to releasably engage the elongated engagement arm, when the elongated engagement arm is out of the second position.

8. The system of claim 7, wherein the fluid connector and the generally tabular assembly includes cooperating means to releasably engage the fluid connector to the generally tabular assembly when the fluid connector is engaged with the elongated engagement arm and rotating joint is in the second position.

9. The system of claim 8, wherein the cooperating means is adapted to provide an audible "click" when the fluid connector is engaged with the elongated engagement arm and the rotating joint is urged into the second position.

10. The system of claim 1, further including a fluid connector removably engageable with the elongated engagement arm and engageable with a remote source of therapeutic fluid, wherein the fluid connector is adapted to slideably releasably engage the elongated engagement arm, when the elongated engagement arm is out of the second position.

11. The system of claim 10, wherein the fluid connector and the generally tabular assembly include cooperating means to releasably engage the fluid connector to the body when the fluid connector is engaged with the elongated engagement arm and rotating joint is in the second position.

12. The system of claim 1, further including a fluid connector removably engageable with the elongated engagement arm and engageable with a remote source of therapeutic fluid, wherein the fluid connector is adapted to releasably engage the elongated engagement arm, when the elongated engagement arm is out of the second position and wherein the fluid connector includes a needle and a needle cover and the elongated engagement arm includes a septum.

13. The system of claim 1, further including a fluid connector removably engageable with the elongated engagement arm and engageable with a remote source of therapeutic fluid, wherein the fluid connector is adapted to releasably engage the elongated engagement arm, when the elongated engagement arm is out of the second position, wherein the fluid connector and the elongated engagement arm are septumless.

14. The system of claim 1, further including a handle assembly having an emplacement needle, the emplacement needle engageable with the axially aligned first fluid channel of the elongated engagement arm.

15. The system of claim 14, further including a plug for assisting with the engagement of the handle assembly to the elongated engagement arm.

16. The system of claim 15, wherein the elongated engagement arm includes a guide member.

17. The system of claim 1, wherein the generally tabular assembly includes a lock for releasably engaging the rotating joint for relesably locking the rotating joint in the second position.

18. A system for subcutaneous delivery of a therapeutic fluid from a remote vessel into the body of a patient, the system comprising:
- a generally tabular assembly having a generally straight elongated cannula extending from a generally flat bottom surface;
- a rotatable joint for engagement with the generally tabular assembly, the rotatable joint having an elongated engagement arm, the elongated engagement arm having a near end and a removed end and a joint body engaged with and integral with the near end of the elongated engagement arm having an axial aligned first fluid channel therethrough, the first fluid channel extending at least partially through the joint body;
- the joint body further having a second interconnecting fluid channel for intersecting with the first axially aligned fluid channel and with a surface of the joint body forming a fluid port thereby;
  - wherein the generally tabular assembly is adapted to engage the rotatable joint so as to provide rotation of the elongated engagement arm in a plane, the plane including the cannula of the generally tabular assembly;
- wherein the elongated engagement arm is moveable between a first position, generally vertical to the generally tabular assembly, wherein the axially aligned first fluid channel is along an axis defining the cannula, to a second position, approximately perpendicular to the first position, wherein the second interconnecting fluid channel is in fluid communication with the cannula;
  - further including a fluid connector removably engageable with the elongated engagement arm and engageable with a remote source of therapeutic fluid, wherein the fluid connector is adapted to releasably engage the elongated engagement arm, when the elongated engagement arm is out of the second position;
    - wherein the fluid connector and the generally tabular assembly include cooperating means to releasably engage the fluid connector to the generally tabular assembly when the fluid connector is engaged with the elongated engagement arm and rotating joint is in the second position; and
  - further including a handle assembly having an emplacement needle, the emplacement needle engageable with the axially aligned first fluid channel of the elongated engagement arm.

19. The system of claim 18, wherein the fluid connector and the elongated engagement arm are septumless.

20. The system of claim 18, wherein the elongated engagement arm and the fluid connector include engagement means, the engagement means including a septum and a needle.

* * * * *